United States Patent
Braun et al.

(10) Patent No.: US 10,088,476 B2
(45) Date of Patent: Oct. 2, 2018

(54) VOLUME RESPONSE SENSORS HAVING ANALYTE CONTROLLED REVERSIBLE CROSSLINKING

(71) Applicants: The Board of Trustees of the University of Illinois, Urbana, IL (US); Vytrace Corporation, Export, PA (US)

(72) Inventors: Paul V. Braun, Savoy, IL (US); Gerald G. Cano, Export, PA (US); Chunjie Zhang, Champaign, IL (US)

(73) Assignees: The Board of Trustees of the University of Illinois, Urbana, IL (US); Vytrace Corporation, Export, PA (US)

( * ) Notice: Subject to any disclaimer, the term of this patent is extended or adjusted under 35 U.S.C. 154(b) by 174 days.

(21) Appl. No.: 15/027,921

(22) PCT Filed: Sep. 29, 2014

(86) PCT No.: PCT/US2014/058074
§ 371 (c)(1),
(2) Date: Apr. 7, 2016

(87) PCT Pub. No.: WO2015/053975
PCT Pub. Date: Apr. 16, 2015

(65) Prior Publication Data
US 2016/0252505 A1    Sep. 1, 2016

Related U.S. Application Data

(60) Provisional application No. 61/887,506, filed on Oct. 7, 2013.

(51) Int. Cl.
*G01N 33/543*    (2006.01)
*G01N 33/542*    (2006.01)
(Continued)

(52) U.S. Cl.
CPC ... *G01N 33/54373* (2013.01); *A61B 5/14532* (2013.01); *G01N 33/542* (2013.01); *G01N 33/544* (2013.01); *G01N 33/66* (2013.01)

(58) Field of Classification Search
CPC .......... G01N 33/543; G01N 33/54366; G01N 33/54373; G01N 33/54353;
(Continued)

(56) References Cited

U.S. PATENT DOCUMENTS 6,187,599 B1    2/2001    Asher et al.
6,201,980 B1    3/2001    Darrow et al.
(Continued)

FOREIGN PATENT DOCUMENTS

WO    98/43086 A1    10/1998

OTHER PUBLICATIONS

Zhang, Jian-Tao et al. "Temperature-sensitive PVA/PNIPAAm semi-IPN hydrogels with enhanced responsive properties." Acta Biomaterialia (2009) 5 488-497, (Year: 2009).*
(Continued)

*Primary Examiner* — Christopher Adam Hixson
(74) *Attorney, Agent, or Firm* — Haukaas Fortius PLLC; Michael H. Haukaas

(57) ABSTRACT

The invention relates to hydrogel and organogel sensors as well as their application to continuous analyte monitoring. The sensor can include a hydrogel or organogel matrix. Standard and inverse designed are provided. In one embodiment, the matrix can include a molecular recognition agent for an analyte (e.g., a glucose analyte), and a volume resetting agent that reversibly binds with the molecular recognition agent. Reversible crosslinks between the molecular recognition agent and volume resetting agent can change the volume of the matrix upon interacting with the analyte via a competitive binding process. In various
(Continued)

embodiments, the invention provides a hydrogel-based glucose sensor and sensors for continuous glucose monitoring. The glucose sensor can be based on a glucose-responsive hydrogel with a volume linearly correlated with glucose concentrations, such as about 0.05-50 mM, under physiological conditions. The invention thus provides a blood glucose monitor suitable for use in clinical settings.

21 Claims, 14 Drawing Sheets

(51) Int. Cl.
    *G01N 33/544*     (2006.01)
    *G01N 33/66*     (2006.01)
    *A61B 5/145*     (2006.01)

(58) Field of Classification Search
    CPC .. G01N 33/5436; G01N 33/544; G01N 33/66; A61B 5/14532
    See application file for complete search history.

(56) References Cited

U.S. PATENT DOCUMENTS

| | | | |
|---|---|---|---|
| 6,773,564 | B1 | 8/2004 | Yugawa et al. |
| 6,835,553 | B2 | 12/2004 | Han et al. |
| 7,105,352 | B2 | 9/2006 | Asher et al. |
| 8,227,254 | B2 | 7/2012 | Lowe et al. |
| 2008/0214912 | A1 | 9/2008 | Cano |
| 2009/0170209 | A1 | 7/2009 | Machauf et al. |
| 2013/0090444 | A1 | 4/2013 | Horgan et al. |

OTHER PUBLICATIONS

Alexeev et al., "High Ionic Strength Glucose-Sensing Photonic Crystal", Analytical Chemistry vol. 75, No. 10, May 15, 2003; published online Apr. 11, 2003; American Chemical Society; pp. 2316-2323.

Asher et al., "Photonic Crystal Carbohydrate Sensors: Low Ionic Strength Sugar Sensing", Journal of American Chemical Society vol. 125, No. 11, Feb. 22, 2003; American Chemical Society; pp. 3322-3329.

Cui et al., "Photonic Crystal Borax Competitive Binding Carbohydrate Sensing Motif", Analyst vol. 134, No. 5, Mar. 2, 2009; The Royal Society of Chemistry; pp. 875-880.

Heo et al., "Long-term in Viva Glucose Monitoring Using Fluorescent Hydrogel Fibers", PNAS vol. 108, No. 33, Aug. 16, 2011; pp. 13399-13403.

Koschinsky et al., "Sensors for Glucose Monitoring: Technical and Clinical Aspects", Diabetes/Metabolism Research and Reviews vol. 17, Mar. 1, 2001; John Wiley & Sons, Ltd.; pp. 113-123.

Lee et al., "Glucose-Sensitive Inverse Opal Hydrogels: Analysis of Optical Diffraction Response", Langmuir vol. 20, No. 8, Mar. 10, 2004; American Chemical Society; pp. 3096-3106.

Lee et al., "Tunable Inverse Opal Hydrogel pH Sensors", Advanced Materials vol. 15, Nos. 7-8, Apr. 17, 2003; Wiley-VCH Verlag GmbH & Co. KGaA, Weinheim; pp. 563-566.

Li et al., "Development of Boronic Acid Grafted Random Copolymer Sensing Fluid for Continuous Glucose Monitoring", Biomacromolecules vol. 10, No. 1, 2009; published online Sep. 12, 2008; American Chemical Society, pp. 113-118.

Song et al., "A Wireless Chemical Sensor Featuring Iron Oxide Nanoparticle-Embedded Hydrogels", Sensors and Actuators B: Chemical, ScienceDirect, vol. 193, 2014, published online Dec. 24, 2013; Elsevier B.V.; pp. 925-930.

Tierney et al., "Determination of Glucose Levels Using a Functionalized Hydrogel-Optical Fiber Biosensor: Toward continuous Monitoring of Blood Glucose in Viva", Analytical Chemistry vol. 81, No. 9, May 1, 2009; published online Mar. 26, 2009; American Chemical Society; pp. 3630-36363.

United States Patent and Trademark Office International Searching Authority, "International Search Report and Written Opinion for International Patent Application No. PCT/US2014/058074", dated Dec. 31, 2014, 17 pgs.

Ward et al., "Polymerized Crystallized Colloidal Array Sensing of High Glucose Concentrations", Analytical Chemistry vol. 81, No. 12, Jun. 15, 2009; published online May 13, 2009; American Chemical Society; pp. 4978-4986.

Zhang et al., "Hydrogel-Based Glucose Sensors: Effects of Phenylboronic Acid Chemical Structure on Response", Chemistry of Materials vol. 25, No. 15, Jul. 9, 2013; American Chemical Society; pp. 3239-3250.

Zhang et al., "Ultrathin Hydrogel Films for Rapid Optical Biosensing", Biomacromolecules vol. 13, 2012; published Dec. 4, 2011; American Chemical Society; pp. 92-97.

\* cited by examiner

VOLUME RESPONSE SENSORS HAVING ANALYTE CONTROLLED REVERSIBLE CROSSLINKING

RELATED APPLICATIONS

This application is a National Stage filing under 35 U.S.C. § 371 of International Application No. PCT/US2014/058074, filed Sep. 29, 2014, which claims priority under 35 U.S.C. § 119(e) to U.S. Provisional Patent Application No. 61/887,506 filed Oct. 7, 2013, which applications are incorporated herein by reference.

GOVERNMENT SUPPORT

This invention was made with government support under Grant No. HDTRA 1-12-1-0035 awarded by the Defense Threat Reduction Agency of the Department of Defense. The government has certain rights in the invention.

BACKGROUND OF THE INVENTION

Diabetes is one of the most common health concerns worldwide. Treatment of diabetes requires frequent and accurate monitoring of blood glucose concentrations. Blood glucose is one of the most important blood analytes, and some sources refer to blood glucose concentration as the "next vital sign". Optimized insulin therapy facilitated by frequent to continuous accurate monitoring of blood glucose concentration coupled with metabolic control is proposed as one way to reduce the risk of chronic diabetes symptoms.

Although not as well appreciated or understood, the stress of traumatic events such as severe physical injury, heart attack, and surgery, can elevate blood glucose concentration in people who did not have diabetes before the traumatic event. This spontaneous elevation is referred to as "stress induce hyperglycemia". Multiple reports have shown a correlation between stress-induced hyperglycemia and increased morbidity and mortality in intensive care units (ICUs). In 2001, it was reported that maintaining blood glucose within a normal range of 80-110 mg/dL (4.4-6.1 mM), often referred to as tight glycemic control (TGC), reduces surgical ICU mortality by 42% (van den Berghe et al., *N Engl J Med.* 2001 Nov. 8; 345(19):1359). It was demonstrated in the same report that "intensive insulin therapy also reduced overall in-hospital mortality by 34 percent, bloodstream infections by 46 percent, acute renal failure requiring dialysis or hemofiltration by 41 percent, the median number of red-cell transfusions by 50 percent, and critical-illness polyneuropathy by 44 percent, and patients receiving intensive therapy were less likely to require prolonged mechanical ventilation and intensive care." In 2006, it was reported that intensive insulin therapy significantly reduced morbidity among all patients in medical ICUs (van den Berghe et al., *N Engl J Med.* 2006, Feb. 2; 354 (5): 449). These benefits have led ICUs to implement TGC protocols, which in turn has led to interest in automated continuous glucose monitors that can provide continuous or nearly continuous monitoring of blood glucose levels.

Intense research efforts have focused on development of continuous glucose sensing technologies (Koschinsky et al., *Diabetes/Metabolism Res. Rev.* 2001, 17, 113-123.). To meet the requirements for continuous glucose monitoring, a sensor must exhibit high precision, accuracy, sensitivity and stability. From a clinical standpoint, the calibration requirements, availability of results, longevity, and robustness should all be considered when assessing the applicability of a sensor. A motivation for linearly responsive sensors includes their ease of calibration, and the potential for high precision, accuracy, little or no hysteresis and consistent sensitivity over the entire sensing range associated with blood glucose levels. Fast response kinetics is a desirable attribute for continuous glucose monitoring to observe blood glucose fluctuations. High stability of the material is also required to ensure consistent sensor performance during a patient's stay in the ICU, which is typically three days.

Many types of technology have been applied to blood glucose measurement, but none has been successfully developed such that it provides a sensor that satisfies the requirements for accurate and continuous glucose monitoring, particularly of patients in hospital intensive care units. Accordingly, there is a need for new and effective continuous glucose measurement technologies. The glucose sensing technology should provide high precision, accuracy, sensitivity, and stability, fast response kinetics and little or no hysteresis.

SUMMARY

The invention provides a gel-based sensor material that responds to an analyte or group of analytes of interest in a mixture that includes a solution, wherein the sensor material changes dimension while in contact with the solution. The sensor material includes a hydrogel or an organogel, and the hydrogel or organogel includes an initially crosslinked gel such that the volume of the material does not shrink when first exposed to an analyte, a volume resetting agent, and a solvent system. In the gel-based sensor material:

a) the crosslinked gel or the volume resetting agent contains moieties on a molecular recognition agent that specifically react to an analyte or group of analytes;

b) the crosslinked gel or the volume resetting agent that does not include the molecular recognition agent contains heteroatom functionalities that reversibly bind to the molecular recognition agent moieties to form reversible crosslinks within the sensor material such that the sensor material shrinks in volume when the volume resetting agent is added to the gel; and c) the solvent system comprises water, an organic solvent, or a combination thereof.

The molecular recognition agent can be specific to the analyte or group of analytes of interest such that an increase in the concentration of the analyte or group of analytes causes the bonds between the molecular recognition agent and the volume resetting agent to break as a function of the concentration of the analyte or group of analytes so that the volume of the hydrogel or organogel increases, and conversely, wherein decreasing the concentration of the analyte or group of analytes causes the bonds between the molecular recognition agent and the volume resetting agent to form as a function of the concentration of the analyte or group of analytes so that the volume of the hydrogel or organogel decreases.

In one embodiment, the crosslinked gel comprises a molecular recognition agent that comprises boronic acid moieties and the volume resetting agent comprises hydroxyl functionalities.

In another embodiment, the crosslinked gel comprises a molecular recognition agent that comprises hydroxyl functionalities and the volume resetting agent comprises boronic acid moieties.

In some embodiments, the molecular recognition agent can comprise a polyacrylamide polymer functionalized with boronic acid moieties.

In some embodiments, the volume resetting agent can comprise 1,3-diol functionalities. For example, the volume resetting agent can be poly(vinyl alcohol) (PVA) or tris-modified poly(acrylic acid).

In some embodiments, the crosslinked gel can comprise 1,3-diol functionalities. For example, the crosslinked gel include PVA or tris-modified poly(acrylic acid).

In some embodiments, the volume resetting agent can comprise a polyacrylamide polymer functionalized with boronic acid moieties.

In some embodiments, the boronic acid moieties of the molecular recognition agent are phenylboronic acid moieties, 3-aminophenylboronic acid moieties, 5-amino-2-fluorophenylboronic acid moieties, or 4-amino-3-fluorophenylboronic acid moieties.

In some embodiments, the hydrogel or organogel includes a cofunctionality compound covalently bound to the molecular recognition agent, wherein the cofunctionality compound comprises one or more of hydroxyl groups, secondary amine groups, tertiary amine groups, or carboxylic acid groups. In various embodiments, the cofunctionality compound is tris(hydroxymethyl)aminomethane, N,N-dimethylethylenediamine, or a combination thereof.

In some embodiments, the sensor material is sensitive to glucose concentrations from about 0.05 mM to about 80 mM, about 0.1 mM to about 60 mM, about 0.5 mM to about 50 mM, or about 0.5 mM to about 30 mM.

In various embodiments, the sensor material reacts to changes in the concentration of glucose within about 15 minutes, within about 12 minutes, within about 10 minutes, within about 5 minutes, or within about 2 minutes within which time the volume of the sensor material stabilizes to a nearly constant volume.

The sensor material can react to changes in the concentration of glucose with little or no hysteresis. The response of the sensor material to glucose can be substantially linear, for example, where the $R^2$ value is >0.85, >0.9, >0.95, >0.97, or >0.99.

In some embodiments, the sensor material comprises like charged colloidal material dispersed throughout the sensor material, wherein the molecular recognition agent, the volume resetting agent, the colloidal material, and the solvent form a hydrogel or an organogel polymerized crystalline colloidal array (PCCA).

In one embodiment, the charged colloidal material forms a uniform ordered array of particles causing the material to diffract light; wherein a) the reflected wavelengths correlate to the spacing of the particles; b) the particle spacing varies with changes in sensor volume so that i) an increase in volume increases particle spacing uniformly causing a red shift in the reflected light, and ii) a decrease in volume decreases particle spacing uniformly, causing a blue shift in reflected light; and c) the shift is related to the concentration of the analyte or group of analytes in the solution.

The particles can be uniformly-sized polystyrene particles having like surface charges. The particles can have a generally uniform diameter of about 50 nanometers to about 300 nanometers.

In additional embodiments, the sensor material can include a holographic pattern causing the material to diffract light; wherein
 a) the reflected wavelength is directly related to the holographic pattern;
 b) the holographic pattern varies with changes in sensor volume so that:
  i) an increase in volume causes a red shift in the reflected light, and
  ii) a decrease in volume causes a blue shift in reflected light; and
 c) the shift is proportional to the concentration of the analyte or group of analytes in the solution.

In various embodiments, the sensor material can include a hydrogel. The invention also provides embodiments where the hydrogel described herein is replaced or augmented with an organogel.

In various embodiments, the sensor material does not shrink upon first contact with an analyte.

The invention also provides a gel-based polymer sensor comprising polymer chains that are pulled closely together by constructed reversible bonding crosslinks of at least two different moieties, each attached to a different polymer chain;
 wherein the gel-based sensor comprises a hydrogel or an organogel;
 the volume of the polymer sensor changes in the presence of an analyte or group of analytes;
 the bonds between the two moieties spontaneously and reversibly break or form in response to changing concentrations of an analyte or group of analytes of interest in solution; and
 a) the sensor volume increases due to elastic expansion manifest from the breaking of bonds as the concentration of an analyte or group of analytes increases, and
 b) the sensor volume decreases due to contraction against an elastic expansion force manifest from the forming of bonds as the concentration of an analyte or group of analytes decreases.

The hydrogel or organogel can include a cofunctionality compound covalently bound to a polymer chain that includes a molecular recognition agent, wherein the cofunctionality compound comprises one or more of hydroxyl groups, secondary amine groups, tertiary amine groups, or carboxylic acid groups. In certain embodiments, the cofunctionality compound is tris(hydroxymethyl)aminomethane, N,N-dimethylethylenediamine, or a combination thereof can be used. The presence of the cofuctionality can improve the stability of the matrix by preventing leaching of a component of the matrix, such as the volume resetting agent.

The sensor can be combined with a means for measuring volume change, wherein the means for measuring volume change relates volume change to concentration of an analyte or group of analytes. The combination can include a fiber optic, a white light source, and/or spectrometer configured to measure a reflected spectrum from the sensor material immersed in a solution containing an analyte or group of analytes of interest, the spectrum representative of sensor volume and thus representative of the concentration of an analyte or group of analytes in the solution.

The invention further provides a method of monitoring changes in the concentration of an analyte or group of analytes comprising contacting the analyte or group of analytes with a sensor described herein, irradiating the sensor with light, and detecting the wavelength of diffracted light, wherein the wavelength of diffracted light corresponds to an increase or decrease in the concentration of the analyte or group of analytes.

The invention yet further provides a method of making an acrylamide hydrogel glucose sensor material that responds to an analyte in solution by changing volume while immersed in the solution in response to the presence of the analyte, wherein the analyte is a saccharide, diol, triol, or tetraol. The method can include:

a. synthesizing a sensor material by mixing a solution that includes acrylamide, N,N'-methylenebis(acrylamide), and an initiator in suitable and effective proportions;
b. exposing the solution to an energy source compatible with the initiator to polymerize the solution;
c. placing the polymerized material in a hydrolyzing solution for a period of time sufficient to hydrolyze amide moieties of the material to carboxylate moieties;
d. removing the material from the hydrolyzing solution and washing the material in water or a saltwater solution to provide a hydrolyzed material;
e. combining the hydrolyzed material and a boronating solution to attach boronic acid moieties to the polymer chains of the material to form a boronated hydrogel, and
f. combining the boronated hydrogel and a poly(vinyl alcohol) (PVA) solution so that PVA binds to the boronic acid moieties to form crosslinks in the hydrogel, thereby pre-shrinking the hydrogel.

The invention additionally provides a method of making an acrylamide hydrogel glucose sensor material that responds to an analyte in solution by changing volume while immersed in the solution in response to the presence of the analyte, wherein the analyte is a saccharide, diol, triol, or tetraol. The method can include:

a. synthesizing a sensor material by mixing a solution that includes acrylamide, N,N'-methylenebis(acrylamide), and an initiator in suitable and effective proportions;
b. exposing the solution to an energy source compatible with the initiator to polymerize the solution;
c. placing the polymerized material in a hydrolyzing solution for a period of time sufficient to hydrolyze amide moieties of the material to carboxylate moieties;
d. removing the material from the hydrolyzing solution and washing the material in water or a saltwater solution to provide a hydrolyzed material;
e. combining the hydrolyzed material and a Tris solution to attach tris(hydroxymethyl)aminomethane moieties to the polymer chains of the hydrolyzed material to form a hydroxyl-containing hydrogel, and
f. combining the hydroxyl-containing hydrogel and a solution of boronic acid-modified polymer so that the hydroxyl groups in the hydrogel bind with the boronic acid groups in the polymer to form crosslinks in the hydrogel, thereby pre-shrinking the hydrogel.

The weight ratio of acrylamide to N,N'-methylenebis (acrylamide) can be about 1:1 to about 1:100, the total mass of acrylamide and N,N'-methylenebis(acrylamide) per 5 g of water can be about 0.1 g to about 2.0 g, and the mass of the initiator can be about 10% to about 0.05% of the total mass of the monomers.

In one embodiment, the weight ratio of acrylamide to N,N'-methylenebis(acrylamide) is about 1:1, about 1:5, about 1:10, about 1:20, about 1:37, about 1:50, about 1:60, about 1:70, about 1:80, about 1:90, or about 1:100. In various embodiments, the total mass of acrylamide and N,N'-methylenebis(acrylamide) per 5 g of water is about 0.1 g, about 0.2 g, about 0.35 g, about 0.5 g, about 0.7 g, about 1.0 g, about 1.4 g, or about 2.0 g. In certain embodiments, the mass of the initiator is about 10%, about 5%, about 1%, about 0.1%, or about 0.05% of the total mass of the monomers.

In one specific embodiment, the invention provides a hydrogel sensor material that responds to glucose in solution by changing dimension while in contact with the solution, wherein the hydrogel comprises:

a) a molecular recognition agent comprising poly(acrylic acid) functionalized with boronic acid moieties that specifically react to glucose;
b) poly(vinyl alcohol) wherein the 1,3-hydroxyl functionalities of the poly(vinyl alcohol) reversibly bind to the molecular recognition agent boronic acid moieties to form reversible crosslinks within the sensor material such that the sensor material shrinks in volume prior to contacting glucose; and
c) a solvent system comprising water and optionally an organic solvent.

The molecular recognition agent can be specific to glucose such that the presence or an increase in a concentration of glucose causes bonds between the molecular recognition agent and the poly(vinyl alcohol) to break as a function of the concentration of glucose so that the volume of the hydrogel increases, and conversely, wherein a decreasing concentration of glucose causes bonds between the molecular recognition agent and the volume resetting agent to form as a function of the concentration of the glucose so that the volume of the hydrogel decreases; and wherein the sensor material does not shrink upon first contact with glucose.

Accordingly, the invention provides a sensor material comprising a solvent, a molecular recognition agent, and a volume resetting agent, wherein the molecular recognition agent is capable of reversibly crosslinking with the volume resetting agent, the molecular recognition agent is responsive to an analyte but does not include the analyte, wherein the analyte can interact with the reversible crosslinks formed by the molecular recognition agent and the volume resetting agent to change the volume or shape of the sensor material (see FIG. 1). The sensor material can be a hydrogel or organogel, depending on the solvent used to form the sensor material. The sensor material can optionally include colloidal particles such as various sub-micrometer diameter colloidal particles.

The sensor material can be a hydrogel specifically designed to identify changes in glucose concentration. When exposed to a solution containing glucose, it can respond by changing volume. If left in the solution and the glucose concentration is changed, the volume of the hydrogel will change accordingly. Thus, by measuring the sensor volume with a calibrated measurement means, glucose concentration can be determined. To make it easier to determine concentration, the sensor material can be configured to contain an optically diffracting element, the dimensions of which can vary according to the volume change of the hydrogel. The diffraction properties of the material then report on the glucose concentration.

When in contact with an analyte, crosslinks in the sensor material formed between the molecular recognition agent and volume resetting agent break as a function of analyte concentration, and the sensor volume increases. When analyte concentration decreases, the crosslinking between the molecular recognition agent and the volume resetting agent increases, and the sensor volume decreases. Volume change can be nearly linear as a function of analyte concentration, for example, over the range of glucose concentration in blood. The sensitivity of the sensor can be increased in specific ranges for better resolution. By measuring the volume of the sensor by a calibrated measurement means, analyte concentration can be determined. Thus, the invention provides blood glucose monitor technology suitable for use in clinical settings.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
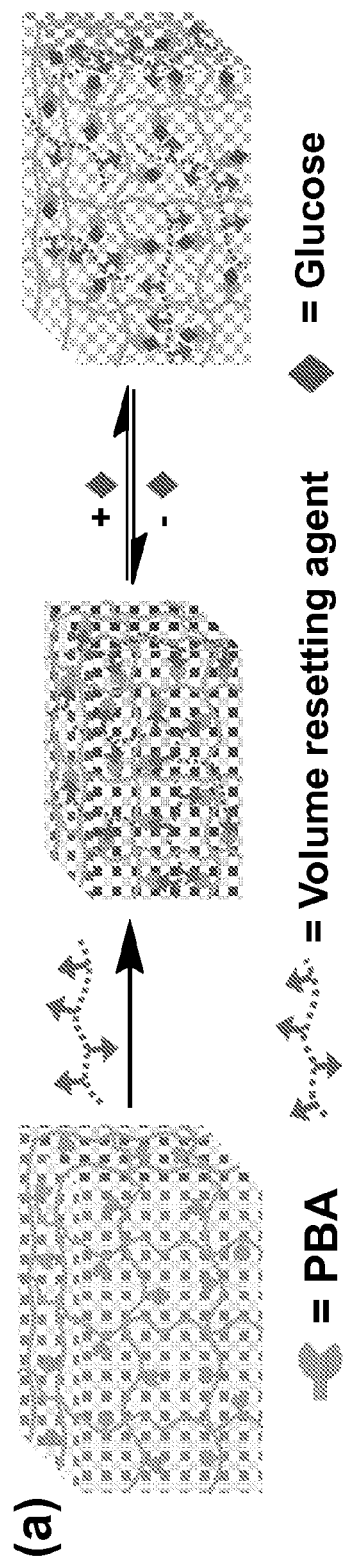
FIG. 1. The design and synthesis of a volume resetting agent-loaded hydrogel glucose sensor material. (a) A schematic representation of the general design protocol of a glucose responsive hydrogel; and (b) synthetic steps for forming a glucose responsive polymerized crystalline colloidal array (PCCA) (steps i-iv), and the sensing mechanism of the PCCA glucose sensor (v). i, Photopolymerization of the polyacrylamide PCCA. ii, Hydrolysis to generate carboxylates on polyacrylamide hydrogel matrix (e.g., about 6-10% of amides hydrolyzed to acids, according to one embodiment). iii, Coupling phenylboronic acid (PBA) moieties and tris(hydroxymethyl)aminomethane (Tris) onto the hydrogel matrix. iv, Crosslinking PBA moieties by the volume resetting agent poly(vinyl alcohol) (PVA). v, Reversible volume response to glucose via dissociation and association of the PBA-PVA-PBA complexes in the presence of glucose.
Figure 1:
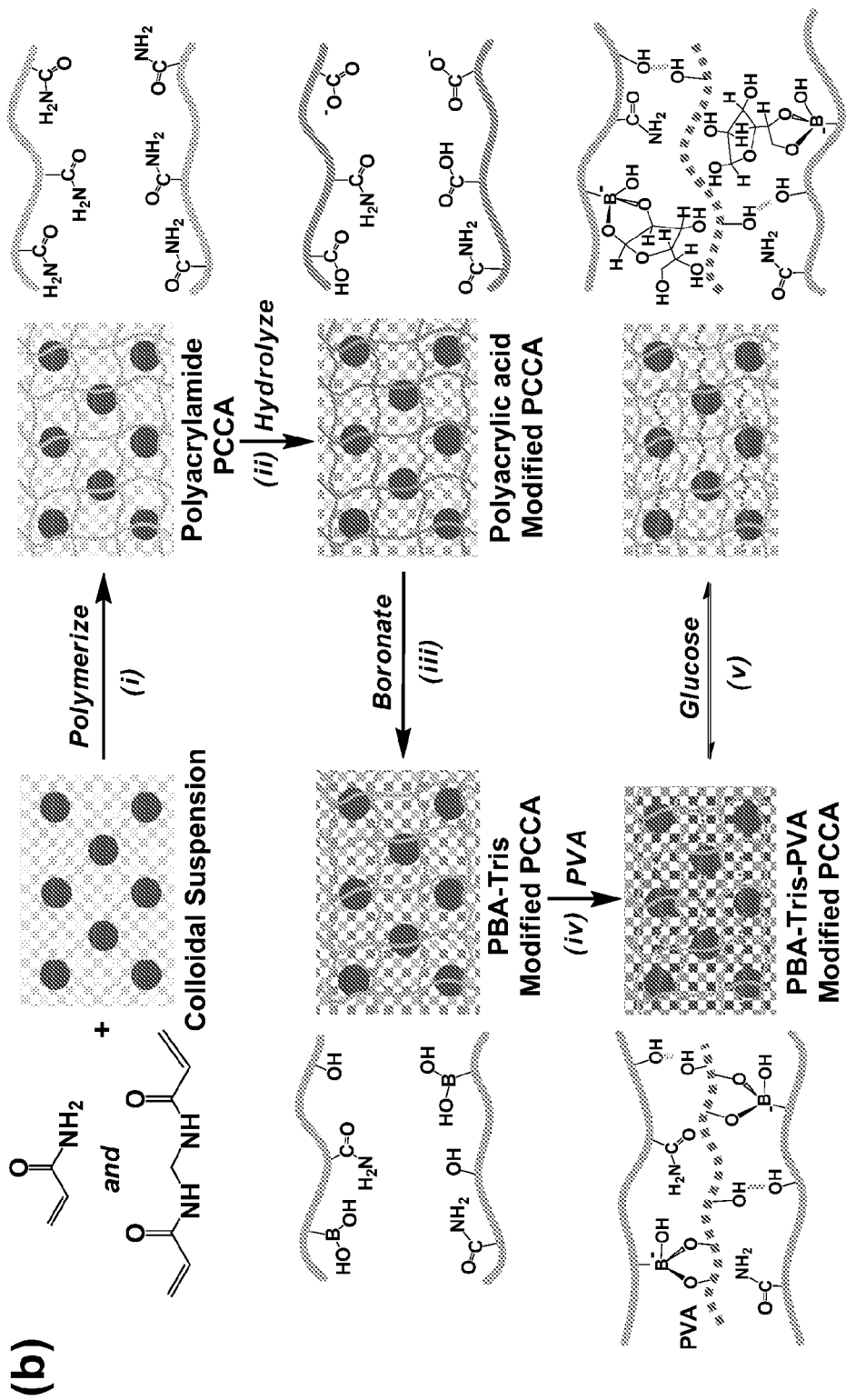

Glucose monitoring, coupled with insulin therapy, can regulate blood glucose levels in diabetic patients and in people who suffer from traumatic events and critical illnesses, for example, patients in the intensive care unit. Real-time continuous knowledge of blood glucose levels is important for making optimal therapeutic decisions, and, as such, continuous glucose monitoring (CGM) technologies have received considerable interest. To maximize their usefulness, CGM devices must provide high precision, accuracy, and sensitivity over the clinically relevant glucose range of 40-700 mg/dL (2.2-38.9 mM), reflecting the requirements for the corresponding sensor materials.

Over the past few decades, enzyme-based electrochemical glucose sensors have witnessed impressive progress toward long-term in vivo applications. However, they have not as yet found acceptance for use in tight glycemic control. As an alternative, or perhaps complimentary to glucose oxidase-based designs, phenylboronic acid (PBA)-based designs can be considered for CGM. PBAs can bind with cis-diols in glucose, leading to fluorescence changes in PBA modified fluorophores and volumetric changes in PBA modified hydrogels. PBA modified hydrogels have a number of attractive attributes for CGM. The hydrogel matrix can immobilize the PBA moieties and can limit biofouling, providing the potential for long-term operation. PBAs also exhibit high operational stability. Finally, the versatility of the boronic acid chemistry offers the flexibility to customize sensor materials to operate over a wide glucose concentration and pH range for a diverse set of applications, including clinical and industrial uses.

Unfortunately, current PBA-modified hydrogels can suffer from nonlinear glucose-induced volume changes due to the complexity of PBA binding with glucose. Accordingly, compositions having improved glucose-PBA interactions are needed to provide both linear response and fast kinetics for analyte monitoring.

Glucose Responsive Hydrogels and Organogels

Glucose responsive hydrogels and organogels are promising candidates for glucose sensing and insulin delivery applications. Molecules that can chemically interact with glucose such as boronic acids, glucose oxidase and lectin can be used as glucose sensing moieties in the synthesis of glucose responsive hydrogels and organogels. The chemical interactions between glucose sensing moieties and glucose can be converted to output signals that are quantitatively detected using different transducers, including electrochemical apparatus, fluorescence molecules, optical devices and the like.

The present invention provides sensors that present a volume change response to variations in an analyte generated by analyte-controlled reversible crosslinks. While the reversible crosslinks are responsive to the presence of the analyte, the analyte itself is not a component of the reversible crosslinks. The volume change can be articulated by including a mechanism in the sensor that causes the diffraction of white light. Addition of an ordered array of colloidal particles is an example of one suitable mechanism. The diffraction produced by the particles produces a color shift that provides a clear indication of the analyte concentration. The color shift is approximately proportional to the glucose concentration. For example, the peak wavelength of the diffraction at the unknown glucose concentration, minus the wavelength at zero glucose concentration, multiplied by a previously determined calibration factor provides the glucose concentration in the unknown. If the sensor has any non-linear response, higher order terms can be added to the equation. The calibration factor is determined by measuring the diffraction wavelength at a minimum of two different known glucose concentrations.

Diffraction means compatible with a volume change sensor include polymerized crystalline colloidal arrays, close packed arrays, and holographically produced gratings. In one embodiment, the sensor is based on a hydrogel. Hydrogel sensors can be used in both high and low ionic strength solutions. Specifically, they can be used in such solutions to measure the concentration of hydroxy acids such as lactate and carbohydrates such as glucose. The hydrogel sensor material includes a molecular recognition agent and a volume resetting agent, which together form reversible crosslinks. For a glucose sensor, the molecular recognition agent can be a polymer having a plurality of boronic acid moieties and the volume resetting agent can be poly(vinyl alcohol) (PVA). The hydrogel sensor can be used for body fluids such as blood, tear fluid, interstitial fluid and other body fluids, solutions that contain glucose, and in the analysis of fermentation.

Embodiments of the invention relate to a sensor material that comprises a hydrogel or organogel capable of volumetric change due to the presence of a molecular recognition agent and volume resetting agent that together form reversible crosslinks, where the molecular recognition agent and volume resetting agent do not contain the analyte but the crosslinking thereof is controlled by or responsive to the presence of an analyte in a solvent. In one embodiment, the sensor is a hydrogel-based glucose sensor material with features suitable for continuous glucose monitoring. In general, the formation of boronic acid-glucose complexes reversibly breaks crosslinks formed from the boronic acid moieties and the volume resetting agent, leading to linear or near-linear expansion of the hydrogel volume. The volume change can be monitored by reading the wavelength of light reflected due the inclusion of a diffracting element in the hydrogel. The hydrogel materials can be tailored to achieve linear fast response, small hysteresis, and minimal signal drift to physiological glucose concentrations under physiological conditions.

Hydrogel-Based Glucose Sensors

Figure 2:
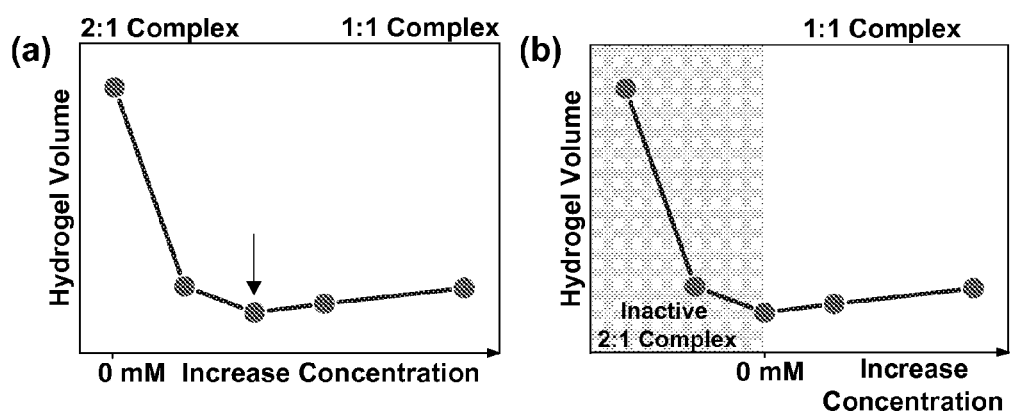
FIG. 2. (a) Volume response of conventional PBA-modified hydrogels over the clinically relevant glucose range. (b) Volume response of volume resetting agent-loaded PBA-modified hydrogels as a function of clinically relevant glucose concentration. 0 mM glucose is the dividing line between the shaded (left) and unshaded (right) region.

Despite many attractive features, the PBA-modified hydrogels to-date suffer from what appears to be an intrinsic limitation, a highly nonlinear glucose-induced volume change, due to the complexity of PBA binding with glucose. Because glucose contains two cis-diols, at low concentrations it can bind with two PBAs generating a 2:1 PBA-glucose complex, forming crosslinks that shrink the hydrogel volume. As glucose concentration increases, the 2:1 complex breaks into two charged 1:1 PBA-glucose complexes resulting in hydrogel swelling. The combination of 2:1 and 1:1 complexes results in a non-linear correlation between the hydrogel volume and glucose concentration, and even over the clinically relevant glucose range, the hydrogel may have the same volume at two different concentrations (FIG. 2a).

We previously studied the response of hydrogels modified with ~20 chemically distinct PBAs (Zhang et al., *Chem. Mater.* 2013, 25, 3239). Out of all these PBAs, the only PBAs that exhibited linear responses over the clinically relevant glucose concentration range had slow kinetics and significant hysteresis upon glucose cycling. Other PBAs that showed fast response kinetics were highly nonlinear within the clinical range. An improved method of tailoring glucose-PBA interactions is needed to provide both linear response and fast kinetics.

To achieve linearity, the coexistence of the 2:1 and 1:1 PBA-glucose complexes needs to be eliminated. Described herein is the use of a volume resetting agent to minimize the competing effects of these two complexes, yielding sensor materials that exhibit a linear and fast response over the clinically relevant glucose concentration range in a simulated physiological environment. To provide an optical readout of the swelling state, a hydrogel was formed into a polymerized crystalline colloidal array (PCCA) photonic crystal (see Holtz and Asher, *Nature* 1997, 389, 829), whose optical reflection wavelength is a function of the hydrogel volume. Because the glucose concentration is determined only by the peak position, and not the intensity of the diffraction, precise and accurate readings can be obtained, even in complex environments.

PBAs have lower affinities to 1,3-diols than 1,2-diols (e.g., glucose), and therefore, 1,2-diol appended molecules can displace preformed 1,3-diol-PBA complexes. Because the 2:1 complex is preferentially formed at low glucose concentrations, most of the PBA functionalities can be crosslinked into 2:1 complexes at zero glucose concentration by adding a 1,3-diol to the hydrogel, such that glucose only leads to expansion of the hydrogel through 1:1 complex formation (FIGS. 1a and 2b). During sensor operation, any added glucose only results in the elimination of preformed 2:1 complexes. The added 1,3-diol is referred to as a 'volume resetting agent'. To accomplish this, the bonding constant of the volume resetting agent with the PBA needs to be appropriate. If the PBA significantly prefers the resetting agent over glucose, glucose could not displace it to form 1:1 PBA-glucose complexes, and the hydrogel volume would not change with glucose concentration, and if the PBA strongly prefers glucose, glucose would simply displace the resetting agent, forming new 2:1 complexes, and the volume would not change until the glucose reached a high concentration.

Polyvinyl alcohol (PVA) was previously used to construct polymer systems that show volumetric response in the presence of glucose following a competitive binding mechanism, demonstrating that the PBA-PVA complexes can be decoupled by glucose. Specifically, these systems were fabricated by layer-by-layer assembly of PBA-containing polymers and PVA (Kikuchi et al., *Anal. Chem.* 1996, 68, 823), by crosslinking PBA-containing polymers and PVA (Cui et al., *Analyst* 2009, 134, 875), or by introducing boric acid into a PVA-based hydrogel (Cui et al., *Analyst* 2009, 134, 875). In contrast with these approaches, in the gel-based sensors described herein, a multivalent volume resetting agent containing multiple chemical functionalities (e.g. either PVA or a boronic acid containing polymer), is added to a preformed gel. The preformed gel contains the chemical functionality that binds to the volume resetting agent (e.g. boronic acid when PVA is added to the gel as the volume resetting agent). Because of the shrinking induced by the volume resetting agent, the resulting composite gel only swells upon interaction with the analyte, and swells linearly over a large range of glucose concentrations, overcoming the non-linear volume response of previous PBA-containing hydrogels. In other words, the sensor materials described herein neither contract or shrink when first introduced to an analyte, nor expand in a non-linear fashion. Previous sensors, which lack the volume resetting agent, exhibit a non-linear response upon introduction of an analyte, which can even include shrinking, followed by expansion as the analyte concentration increases.

Formation of the PBA-modified hydrogel PCCA involves three steps (FIG. 1b); polymerization of acrylamide monomers which constitute part of a crystallized polystyrene colloidal suspension, partial hydrolysis of the resulting polyacrylamide (PAAm) hydrogel matrix to create carboxylate sites, and boronation to attach the PBA functionalities. During boronation, Tris, which primarily serves to localize the PVA chain through hydrogen bonding, but also has some resetting agent characteristics, is incorporated into the hydrogel matrix. The volume resetting agent PVA is then diffused into the hydrogel, where it binds with the immobilized PBAs, forming crosslinks and reducing the hydrogel volume. This final sensor material is denoted PBA-Tris-PVA PCCA.

Figure 3:
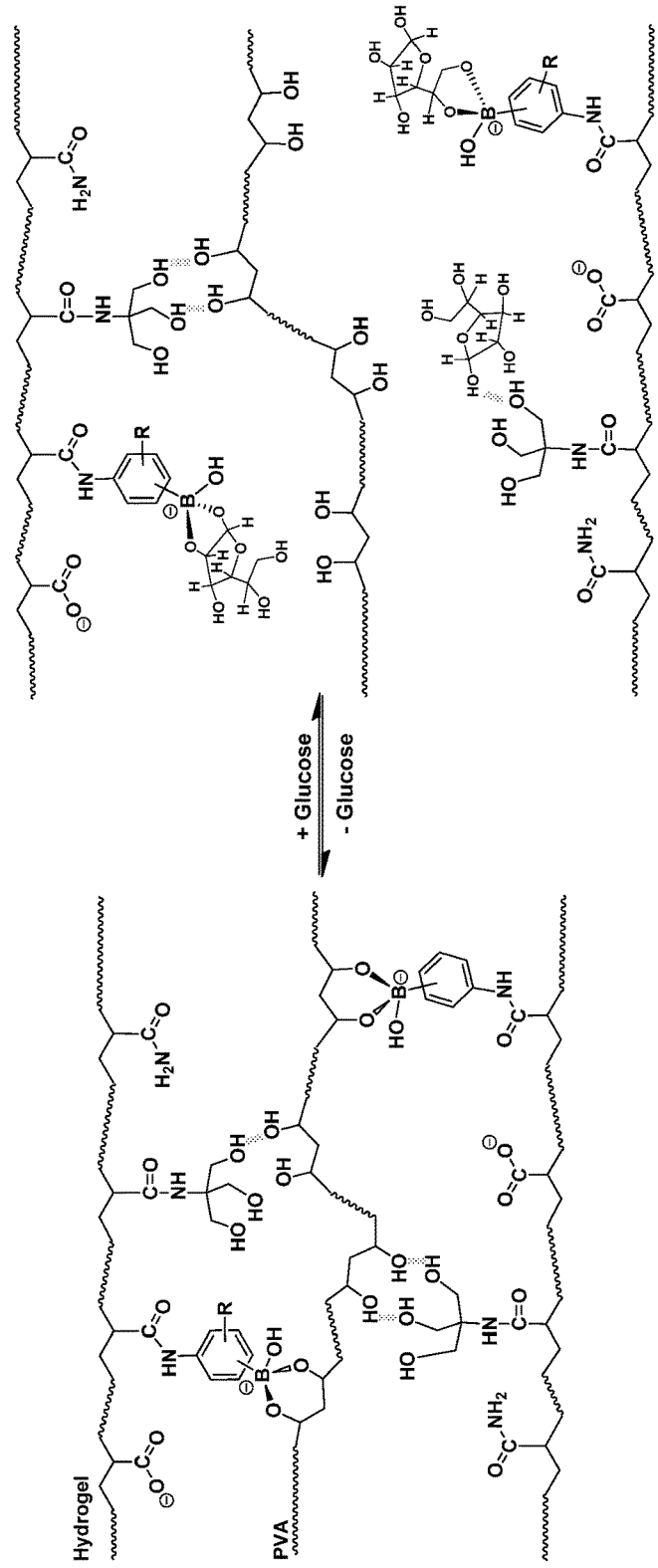
FIG. 3. Chemical structure of the hydrogel matrix of PBA-Tris-PVA PCCA including the reversible crosslinks that are broken by glucose, according to one embodiment.

When exposed to glucose, some of the PBA-PVA-PBA crosslinks inside the hydrogel matrix are replaced by 1:1 PBA-glucose complexes, leading to a hydrogel volume expansion and commensurate redshift of light diffracted by the PCCA (the detailed chemical structure of the PBA-Tris-PVA hydrogel is provided in FIG. 3). The diffracted wavelength shift is linear over the clinically relevant glucose range, and eventually saturates at high glucose concentrations (greater than 60 mM, e.g., approaching 100 mM) once the majority of the PBA-PVA-PBA crosslinks are replaced by 1:1 PBA-glucose complexes.

Figure 4:
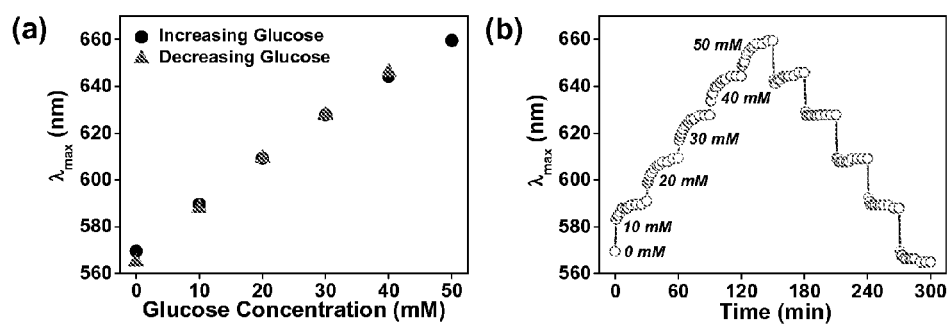
FIG. 4. (a) Diffracted wavelength during a pre-cycling test between 0 and 50 mM glucose. (b) Diffracted wavelength as a function of time during the glucose concentration sweep.

To fully cover the clinically relevant glucose range, a cyclic sweep of glucose concentration between 0 and 50 mM was performed under simulated physiological conditions (pH 7.4 phosphate buffer with physiological salinity). The same sweep was performed on the same sensor material one day before the test to ensure the observed sensor performance was close to the equilibrated state (FIG. 4). The response of the PBA-Tris-PVA PCCA linearly correlates to glucose concentration ($R^2$=0.998) (FIG. 5a-b). At 10 mM glucose, the hysteresis of this sensor is 1.6 nm, which corresponds to an error of only ~0.9 mM glucose. Minimal hysteresis is provided by the rapid response kinetics (FIG. 5c). For this design, in a 0-10 mM step, the time needed to reach 90% of the equilibrated wavelength ($t_{90}$) is ~7 minutes while for 30-40 mM step, $t_{90}$ is ~12 minutes. A faster hydrogel system is described herein below.

Along with hysteresis, minimal drift is also important. If PVA leaches from the hydrogel, significant drift may occur, and considerable drift in fact was observed when the PVA was not well localized in the hydrogel (see FIG. 6). Drift was largely eliminated by adding Tris to the hydrogel. Hydrogen bonding between Tris and PVA can prevent PVA leaching (see Example 1, Section 1.8). The Tris-containing sensor shows good stability, with only a few nanometer drift over 3 days in 5 mM glucose solution under simulated physiological conditions (FIG. 5d). Thus, the invention provides a method for reducing signal drift and for reducing the leaching of a volume resetting agent, and compositions that include Tris as a drift-reducing agent, wherein the Tris can be covalently bonded to polymers of the gel matrix. The amount of Tris used is typically about 1 to about 50 times the amount of boronic acid-containing polymers of the gel matrix (as a molar ratio). In some embodiments, the amount of Tris is about 20, 30, or 40 times the molar amount of the boronic acid-containing polymers of the gel matrix.

For all concentration steps, the response kinetics are faster upon decreasing glucose concentration relative to increasing glucose concentration. This property may be due to the low concentration of PBA and high concentration of PVA repeating units inside the hydrogel (see Example 1, Table 2). The hydrogel expands when free glucose reacts with a PVA-PBA complex, and contracts when a PVA repeating unit complexes with PBA. Because the PBA concentration inside the hydrogel is low, the PBA-PVA-PBA complex is also present at a low concentration. This results in the relatively slow kinetics of glucose induced dissociation of this complex during increasing glucose concentration. When glucose departs from the PBA-glucose complex in the decreasing concentration steps, the high concentration of PVA repeating units leads to the fast complex formation kinetics with PBA (see Example 1, Section 1.10 for a more extensive discussion on the kinetics). This sensor design operates at physiological pH, lower than the $pK_a$ of the corresponding boronic acid, 3-aminophenylboronic acid ($pK_a$=8.5 when conjugated in the hydrogel), possibly because the PBA-PVA complex stabilized by the hydrogel has a $pK_a$ value close to physiological pH.

Figure 7:
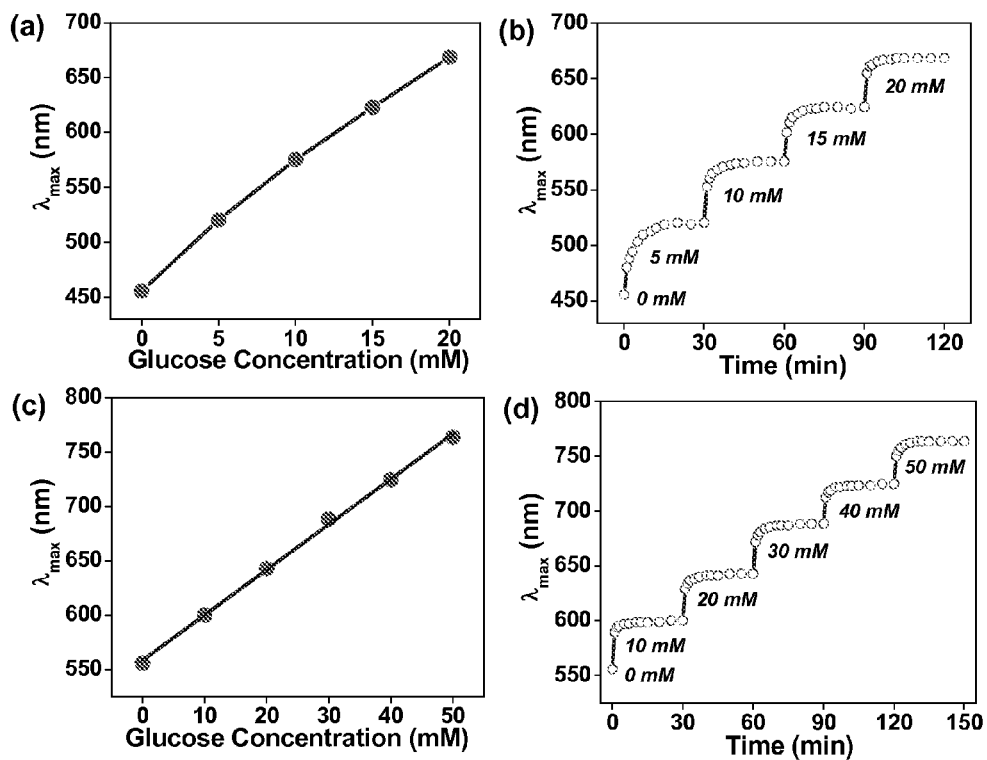
FIG. 7. Glucose sensing performance of optimized photonic hydrogel sensors. (a) Diffracted wavelength shift of 5A2FPBA-Tris-PVA PCCA optimized for responding at low glucose concentrations as a function of glucose concentration. Lines connecting data points are aids to the eye. (b) Temporal evolution of the diffracted wavelength shift of the material in (a). (c) Diffracted wavelength shift of 3APBA-N,N-dimethylethylenediamine-PVA PCCA optimized for rapid kinetics, as a function of glucose concentration. Line is a linear fit. (d) Temporal evolution of the diffracted wavelength of the material in (c). All tests were performed in pH 7.4 phosphate buffered glucose solutions at 37° C. $\lambda_{max}$ is the wavelength corresponding to the maximum of the first order diffraction peak.

The glucose sensing performance can be further tailored by molecular design during the hydrogel synthesis, thus offering flexibility in controlling the sensitivity, dynamic range, and response kinetics. The sensitivity, which is defined as the wavelength shift for a given glucose concentration change, can be controlled through the PBA loading and the PBA-glucose interaction strength. The PBA-Tris-PVA PCCA with more PBA (FIG. 5e) (approximately twice the PBA concentration of the PCCA of FIG. 5b) has higher glucose sensitivity than an otherwise identical PBA-Tris-PVA PCCA with lower PBA content (FIG. 5b). By using a more diol-reactive PBA, 5-amino-2-fluorophenylboronic acid (5A2FPBA), instead of the less reactive 3APBA, higher sensitivity (12 nm/mM glucose over the range of 0-10 mM glucose) is achieved (FIG. 7a vs. Figure Se). A method for improving response kinetics is to replace Tris with N,N-dimethylethylenediamine ($NH_2$—$CH_2CH_2$—$N(CH_3)_2$). The complex formed between immobilized 3APBA and tertiary amine is more reactive with glucose than 3APBA at physiological pH, leading to a sensitivity of 4.2 nm/mM glucose from 0-50 mM glucose and fast response kinetics ($t_{90}$=3 minutes from 0-10 mM glucose) (FIGS. 7c and 7d). The sensor response is not diffusion limited, as the response time of a 30 μm thick sensor is similar to that of a 10 μm thick sensor.

Figure 8:
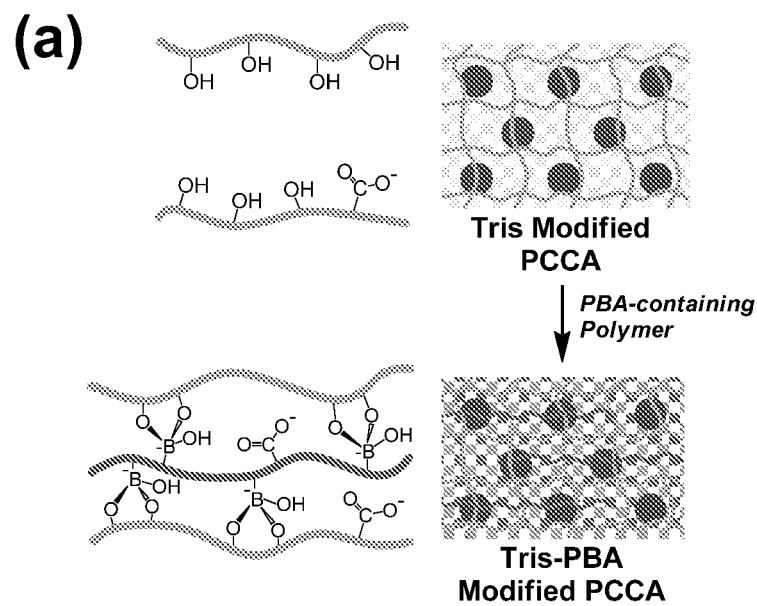
FIG. 8. Sensor material based on an inverse design. (a) Tris-modified polyacrylamide PCCA is associated with a PBA-containing polymer as the volume resetting agent. (b) Diffracted wavelength as a function of glucose concentration of the sensor material depicted in (a). Line is a linear fit. The tests were performed in pH 7.4 phosphate buffered glucose solutions at 37° C. $\lambda_{max}$ is the wavelength corresponding to the maximum of the first order diffraction peak.
Figure 8:
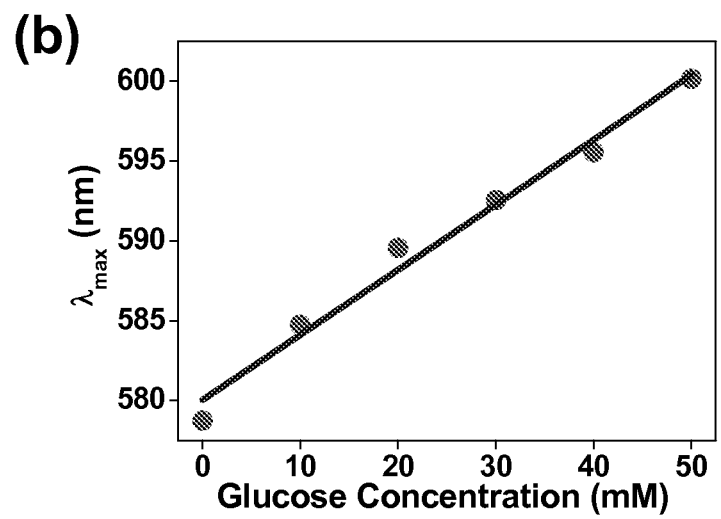

To demonstrate the universality of the resetting agent concept, a sensor based on an inverse design of FIG. 1 was fabricated (see FIG. 8a and the description below). Tris was attached to the hydrogel matrix, and a PBA-containing polymer was added to the Tris-modified hydrogel matrix as the volume resetting agent. The 1,3-diols in Tris bind with the PBA functionalized polymer, forming crosslinks, altering the hydrogel into a contracted state. As shown in FIG. 8b, the resulting hydrogel sensor material shows a nearly linear redshift with increasing glucose concentration. Similar to the design in FIG. 1, structural parameters including hydrolysis time, 1,3-diols, types of PBAs, and PBA content in the volume resetting agent can be varied to modify the sensing performances.

Thus, we describe and have demonstrated a new glucose sensor materials design that exhibits a linear fast response as well as minimal hysteresis and signal drift under physiological conditions. Two important elements of the sensor material are the PBA-modified hydrogel matrix and the volume resetting agent PVA. The inverse design is also effective as a linear fast response sensor. The volume resetting agent effectively eliminates the coexistence of the 2:1 and 1:1 PBA-glucose complexes, which is responsible for the previously observed nonlinear response of PBA-based hydrogel sensors to glucose. After introducing the volume resetting agent, glucose primarily forms 1:1 complexes with immobilized PBAs, leading to a glucose-dependent expansion of hydrogel volume and concomitant redshift of diffracted light by the embedded photonic crystal. This sensor concept offers considerable flexibility to achieve the desired sensitivity and response kinetics. The concept can be used for the detection of other analytes as well.

Sensor Technology Applications

The hydrogels and organogels described herein can be used to prepare a variety of sensors that can be used to perform a variety of different sensing operations. Several examples are as follows.

The sensors experience a volume change that can produce a light return in the visible spectrum. The sensors described herein can produce a light signal that corresponds to a concentration of dissolved glucose in a solution or in a colloidal mixture such as blood. For example, the light signal can be proportional to the concentration of dissolved glucose in blood.

Sensing by Bragg Diffraction.

The hydrogels or organogels described herein can be Bragg diffraction-type sensors. A "diffraction grating" is required to produce diffraction, a phenomenon that occurs when the grating is illuminated with light. When light is directed onto the grating, a band of wavelengths of light is reflected, the wavelengths of which are based upon the dimensional characteristics of the grating; the remainder of the light is transmitted through the sensor.

Figure 10:
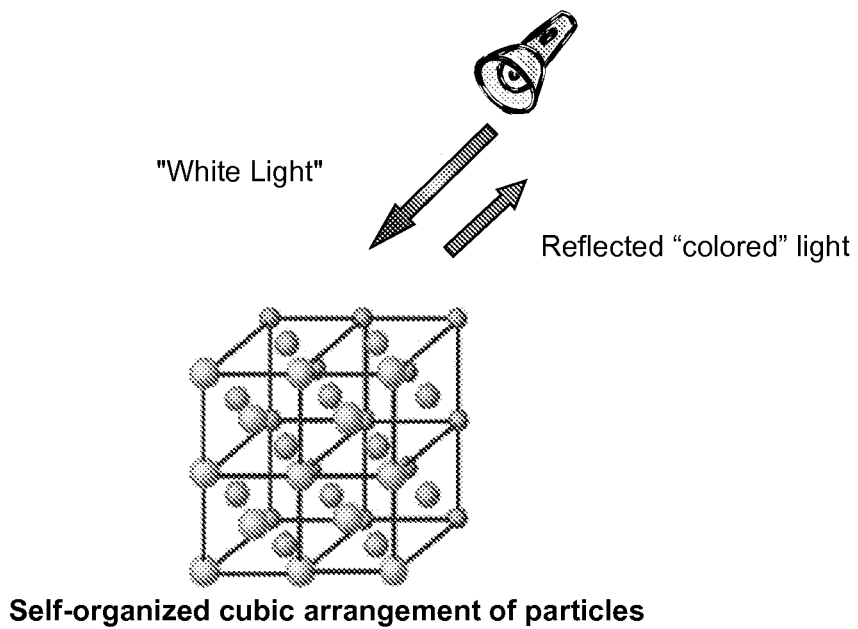
FIG. 10. A schematic representing Bragg diffraction where a self-organized cubic arrangement of particles is exposed to white light and in return the particles reflect light of a specific wavelength or set of wavelengths, according to an embodiment.

A diffraction grating in a hydrogel can be created in at least one of two ways. A photographic method produces a hologram in the hydrogel, for example, by use of a holographic film. A second method uses like-charged colloidal particles to establish a self-organized array of particles in the hydrogel in one of two ways: a polymerized crystalline colloidal array (PCCA) or a close packed array (see FIG. 10). Colloidal particles can be used to establish a self-organized array of particles in the hydrogels. Changes in the volume of the hydrogel produce corresponding changes in the diffraction grating, and thus changes in the diffracted light.

Described herein is a new hydrogel technology that uses volume change phenomena and spectral shift phenomena as the basis for a true sensor. The chemistry of the sensor material provides a controlled linear response to glucose concentration change, operates over a broad range of glucose concentrations, provides a large spectral change response that is easily measured, does not have hysteresis, and has a fast time response to glucose concentration changes. In one embodiment, the chemistry relates to pre-shrinking the hydrogel sensor material through the use of a volume resetting agent such as poly(vinyl alcohol) (PVA) or tris-modified poly(acrylic acid). The amino group on Tris is conjugated to a carboxylic acid group of a volume resetting agent. Any desired proportion of acid moieties can be converted to amides (e.g., 10%, 25%, 50%, or 75%) by adjusting the amount of Tris added to the carboxylic acid-containing polymer (e.g., PAA).

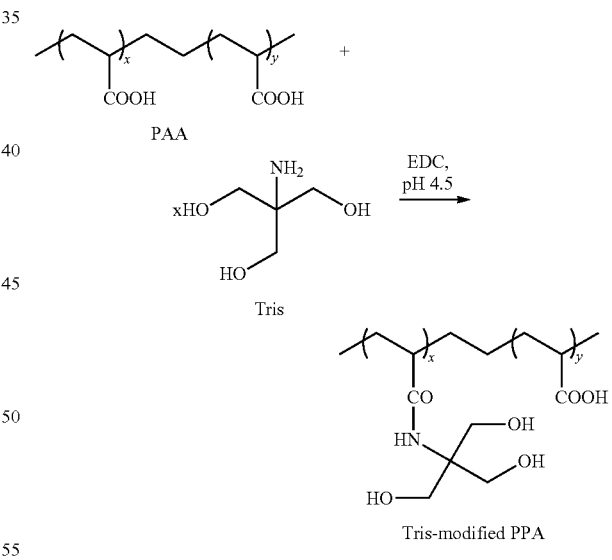

For example, a portion of the carboxylic acid in PAA (i.e., x/(x+y), is converted as shown in the above reaction. The ratio of x/(x+y) can range from about 1% to about 100%. The pre-shrinking is characterized by the agent forming temporary crosslinks involving the boronic acid moieties attached to the hydrogel.

Sensors for Continuous Glucose Monitoring

The concept and design of the sensors and methods described herein are directed to a high performance sensor that is capable of continuous glucose monitoring in body fluids. Current sensor technologies generally suffer from problems in both materials design and sensing operations. The sensor materials can suffer from nonlinear response, slow response kinetics, poor output signal strength, poor stability, high working pH, and the like. Their sensing operations are inadequate because they can require a warm-up period (up to hours) prior to use, require complicated and frequent calibration, and provide insufficient accuracy. The sensor design described herein, which is based on Bragg diffraction, solves many critical problems in existing glucose sensor technologies, in particular, those based on diffraction, and meets the key elements for continuous glucose monitoring. The following seven aspects of a sensor elements are important for effective continuous glucose monitoring.

1. The chemical interactions between glucose and the photonic crystal transducer induce a significant or detectable volume change in the PCCA that is manifest as a wavelength shift. The wavelength shift (change in color) is more reliable as a signal to report glucose concentrations in physiological environments than fluorescence intensity, which is the parameter measured in fluorescence-based glucose sensors. The significant or detectable large wavelength shift is also more advantageous than changes in electrochemical signals, e.g., small current and voltage changes, which are often accompanied by significant electrical "noise" that is found in most electrochemical glucose electrodes. The unique chemistry of the photonic crystal glucose sensors described herein enables the sensor precision and accuracy needed for clinical applications.

2. Boronic acids are used as sensing moieties in the glucose responsive hydrogels instead of proteins such as glucose oxidase, glucose dehydrogenase and lectin. Boronic acids are a family of molecules that show great stability and significant affinity to glucose. The stability of boronic acid moieties contributes to the stability, precision and accuracy of the sensor design. The affinity of boronic acid to glucose further enables the sensitivity of the sensors described herein.

3. A linear or nearly linear response under physiological conditions is achieved by incorporating a polyol such as PVA in the boronated hydrogel. Most developmental glucose responsive systems have nonlinear response, which leads to complication in calibration, decreased sensitivity, or even inapplicability as glucose sensors. The sensors described herein can exhibit highly linear response curves ($R^2 > 0.97$).

4. Fast response kinetics under physiological conditions. The sensors described herein demonstrate a response time of about 5 minutes or less for most glucose fluctuations, which enables frequent to continuous reading of blood glucose concentrations. In addition, the sensor does not require a "warm-up" step prior to use, whereas natural protein-based glucose sensors often require a warm-up step, often hours in length of time.

5. Very small hysteresis under physiological conditions. Sensors described herein were tested using glucose solution titrations in 10 mM steps from 0-50 mM and back to 0 mM glucose. There was a trivial lag in diffraction wavelength for any specific glucose concentration, indicating little or no hysteresis in the sensors. This superior property of the sensors thus satisfies one of the most important requirements for continuous glucose monitoring.

6. High stability under physiological conditions. A static test showed a stable output signal over 72 hours, which is an advantageous sensor lifetime for continuous glucose monitoring. This feature reduces the need for calibration during use and ensures suitable sensor lifetime for clinical purposes.

7. Large output under physiological conditions. Many existing glucose sensing technologies suffer from low output signals that can be obscured or distorted by interference from both the sensing environment and operating apparatus. The interference can be caused by a physiological pH that is too low for some sensing chemistries, and/or by interference caused by high physiological ionic strength (~150 mM NaCl) that may screen the sensor response. The low output signal of existing sensing devices reduces their precision, accuracy and sensitivity. The sensors described herein show large output signals that can be accurately captured by a spectrometer, for example, a reflection wavelength shift of at least 2 nm/mM glucose and a peak intensity greater than about 5%, greater than about 10%, or greater than about 15% of the incident light. The output signal (=wavelength shift/ glucose concentration) can be tuned to detect both high and low glucose concentrations (hyperglycemia and hypoglycemia respectively) with high sensitivity.

The performance of the hydrogel and organogel sensors described herein is such that the glucose sensor material can be used for intermittent or continuous measurement of glucose in medical patients. The sensors are applicable for any glucose measurement that involves a body fluid, such as measuring blood glucose levels for monitoring or diagnosing diabetes. Thus, the glucose sensor material can be used for measuring glucose in blood, interstitial fluid, or tear fluid. The glucose sensor material can also be used for measuring glucose in blood of medical patients who experience acute events and are cared for in an intensive care unit of a hospital.

In one embodiment, a procedure for using the sensor material is as follows. Sensor material is placed at the tip of a fiber optic having a diameter 1 mm or less. The tip of the fiber optic can be protected by a dialysis membrane. The fiber optic can be any suitable length such as 6-18 inches or about 1 to about 9 feet long. The fiber optic can be attached to a monitor having a read-out screen. Inside the monitor is a "white light" source that illuminates the sensor material through the fiber optic. The tip of the fiber optic can reside in a blood vessel of a patient. The sensor material can continuously respond to changes in glucose concentration in the patient. Based on the glucose concentration, the narrow band of light that reflects off the sensor material is returned to the monitor and can be measured by a spectrometer. The spectral reading is then converted to a glucose concentration and can be displayed on the screen.

Compositions and Methods of the Invention

The invention provides sensors and methods to synthesize sensors. The sensors can experience a near-linear volume change response to an analyte or group of analytes in a solvent, for example, glucose in blood. The invention also provides methods for the conversion of the hydrogel volume change to a light output signal that undergoes a wavelength change. By inclusion of a diffraction grating linked to the volumetrically changing hydrogel structure, volume change is expressed as a diffracted wavelength shift due to variation in lattice spacing of the grating.

The invention further provides a measurement system that responds to the diffracted wavelength shift described herein. A spectrometer that detects the diffracted wavelength shift can be connected with the sensor material that contains an embedded optically diffracting element.

The sensor hydrogel can have a thickness from nanometers (which can be analyzed using, for example, a capacitance readout) to micrometer scale, depending on the fabrication technique. Measurement of a capacitance readout can be carried out by various techniques known to those of skill in the art, for examples, as described in U.S. Pat. No. 6,201,980 (Darrow et al.). Alternatively, magnetic permeability can be used to report the volume change of a stimuli responsive hydrogel or organogel (see Song et al., *Sensors and Actuators B: Chemical* 193 (2014), 925-930).

Various glucose sensor materials for use under physiological conditions are described and their performance is demonstrated. The sensors have been successfully evaluated under physiological conditions including a pH 7.4 phosphate buffer solution with physiological salinity at 37° C. Blood serum with pH 7.4 at 37° C. has also been used for evaluating the glucose sensing technology.

Various polymers can be used to make the glucose sensor material. Typically, a polyacrylamide hydrogel is synthesized by photopolymerization followed by a hydrolysis of amide moieties to create carboxylate sites for attaching the molecular recognition agent. The molecular recognition agent can be a boronic acid or a mixture of boronic acids. After boronation, a volume resetting agent, e.g., poly(vinyl alcohol) (PVA), can be incorporated to the hydrogel.

The sensitivity of the glucose sensor material can be varied by using different boronic acids and/or by incorporating co-functionalities, for example, by ionically or covalently bonding Tris to the polymer of the hydrogel. The high sensitivity to glucose, which is expressed as the large volume change per unit of glucose concentration, is valuable for situations where a small variation of glucose concentration needs to be detected. A low sensitivity to glucose is needed when the glucose concentration fluctuates over a large range.

The response kinetics of the sensor material can be varied by using different boronic acids and/or by incorporating co-functionalities. The signal drift of the sensor material can be reduced by incorporating co-functionalities, and the small signal drift reduces the need for calibration during operation.

Accordingly, the invention provides a gel-based sensor material that responds to an analyte or group of analytes in a fluid by changing dimension while in contact with the fluid, wherein the sensor material comprises a hydrogel or organogel comprising:

a) a molecular recognition agent that reacts specifically to an analyte or group of analytes, wherein the molecular recognition agent is a polymer having pendant boronic acid moieties, wherein the polymer can be a water-soluble or organic-soluble polymer;

b) a volume resetting agent, wherein the volume resetting agent is an oligomer (e.g., a compound having 5-50, typically an average of about 10 or 20, repeat units) or a polymer that comprises side-chain heteroatom functionalities, such as 1,3-diol functionalities, that reversibly bind to the boronic acid moieties of the molecular recognition agent to form crosslinks within the hydrogel or organogel such that the gel shrinks in volume; and c) a solvent such as water, an organic solvent, or a combination thereof.

The gel-based sensor material can optionally further include charged colloidal microparticles or nanoparticles wherein the molecular recognition agent, the volume resetting agent, and the charged colloidal microparticles or nanoparticles, form a hydrogel polymerized crystalline colloidal array (PCCA).

The molecular recognition agent can be specific to the analyte or group of analytes of interest such that an increase in the concentration of the analyte or group of analytes causes the bonds between the molecular recognition agent and the volume resetting agent to break as a function of the concentration of the analyte or group of analytes so that the volume of the hydrogel increases, and conversely, wherein decreasing the concentration of the analyte or group of analytes causes the bonds between the molecular recognition agent and the volume resetting agent to form as a function of (or in proportion to) the concentration of the analyte or group of analytes so that the volume of the hydrogel decreases, and the wavelength of light diffracted from the hydrogel sensor material corresponds to the concentration of the analyte or group of analytes.

Thus, increases in volume and/or decreases in volume of the sensor material can be a near-linear function of the analyte concentration over a concentration range of interest.

In some embodiments, the hydrogel can be exchanged for an organogel by replacing some or all of the water with an organic solvent such as dimethyl sulfoxide, dimethylformamide, ethanol, N-methyl-2-pyrrolidone, tetrahydrofuran, and the like.

The gel-based sensors include a solvent system. The solvent system can be water, an organic solvent, or a combination thereof. A gel-based sensor wherein 50% or more of the solvent system by volume is water is considered a hydrogel. A gel-based sensor wherein greater than 50% of the solvent by volume is an organic solvent is considered an organogel. The hydrogels described herein can be prepared as organogels by adding organic solvent, reducing the amount of water used in the solvent system, or combinations thereof.

The polymer of the molecular recognition agent can be a modified polyacrylamide. In other embodiments, the water-soluble polymer of the molecular recognition agent can be synthesized from at least one of or a mixture of acrylamide, (hydroxyethyl)methacrylate, 2-hydroxyethyl acrylate, [2-(methacryloyloxy)ethyl]trimethyl-ammonium, 3-sulfopropyl acrylate salt, 2-(dimethylamino)ethyl acrylate, 2-(diethylamino)ethyl acrylate, acrylic acid, poly(ethylene glycol) acrylate, N-alkylmethacrylamides, N-alkylacrylamides, N,N-diacrylamides, acrylic acid, methacrylic acid, 2-acrylamido-2-methyl propane sulfonic acid, N,N-dialkylaminoethyl methacrylate, methacryloyloxyethyltrialkylammonium bromide, 2,3-dihydroxypropyl methacrylate, 2-(diisopropylamino)ethyl methacrylate, 2-gluconamidoethyl methacrylate, 2-hydroxypropyl methacrylate, 2-lactobionamidoethyl methacrylate, 2-(methacryloyloxy)ethyl succinate, carboxybentaine methacrylate, 1-ethyl-3-(2-methacryloyloxy ethyl)imidazolium chloride, 2-methacryloyloxyethyl phosphate, 2-(methacryloyloxy)ethyl-trimethylammonium chloride, sulfobetaine methacrylate, 2-sulfatoethyl methacrylate, poly(ethylene glycol) methyl ether acrylate, di(ethylene glycol) ethyl ether acrylate or a similar monomer compatible with forming a glucose sensor.

The boronic acid moieties of the molecular recognition agent can be covalently bonded to the polymer of the molecular recognition agent. Examples of boronic acid compounds that can be used to form the pendant boronic acid moieties include but are not limited to at least one or a mixture of 2-aminophenylboronic acid, 3-aminophenylboronic acid, 4-aminophenylboronic acid, 4-amino-3-fluorophenyl boronic acid hydrochloride, 4-amino-3-nitrophenyl boronic acid, 3-amino-4-methylphenylboronic acid, 2-amino-5-fluorophenyl boronic acid, 2-amino-4,5-difluorophenylboronic acid, 3-amino-4-fluorophenylboronic acid, 3-amino-5-cyanophenylboronic acid, 3-amino-5-nitrophenylboronic acid, 2-amino-4-cyanophenylboronic acid, 2-aminomethyl-4-fluorophenylboronic acid, 2-aminomethyl-5-nitrophenylboronic acid, 2-aminomethylphenylboronic acid, 3-aminomethylphenylboronic acid, 4-aminomethylphenylboronic acid, 2-aminomethyl-5-fluorophenylboronic acid, 5-aminomethyl-2-fluorophenylboronic acid, 5-amino-2-fluorophenylboronic acid, 2-aminopyridine-5-boronic acid, 2-aminopyridine-3-boronic acid, 2-aminopyridine-5-boronic acid, other boronic acid containing compounds containing carboxylate, thiol, azide, or alkyne groups, or other boronic acid containing compounds compatible with forming a glucose sensor. The functional groups (e.g., amino, fluoro, nitro, methyl, cyano, etc.) of the phenyl moieties of this paragraph can be the R groups of shown in FIG. 3. While FIG. 3 shows the (phenyl)boronic acid moieties conjugated to a gel polymer via amide linkages, polymers having other linkages may be prepared, as would be recognized by one of skill in the art. Suitable linkages include esters, reversed amides, disulfides, or triazoles as a result of click chemistry reactions. Examples of such reactions include:

(a) Ester Linkages:

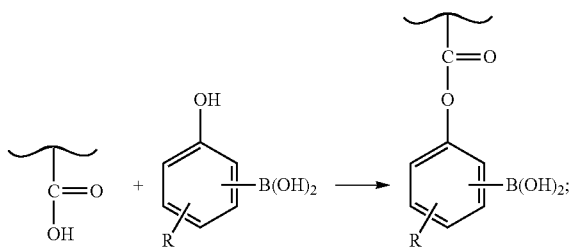

(b) Reversed Amide Linkages:

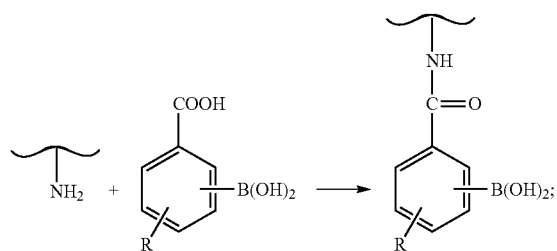

(c) Disulfide Linkages:

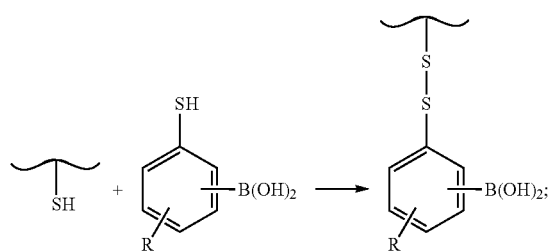

or (d) Click Chemistry Linkages:

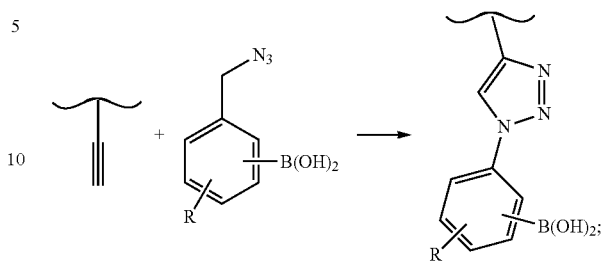

where the R groups can be a phenyl substituent recited above.

In some embodiments, the boronic acid moieties of the molecular recognition agent can be included in the molecular recognition agent by polymerization with the monomers of the water-soluble polymer that forms the molecular recognition agent. Examples of boronic acid compounds that can be used include but are not limited to at least one or a mixture of 2-acrylamidophenylboronic acid, 3-acrylamidophenylboronic acid, 4-acrylamidophenylboronic acid, 4-acrylamido-3-fluorophenylboronic acid, 4-acrylamido-3-nitrophenylboronic acid, 3-acrylamido-4-methylphenylboronic acid, 3-acrylamido-4-fluorophenylboronic acid, 5-acrylamido-2-fluorophenylboronic acid, 2-acrylamido-5-fluorophenylboronic acid, 2-acrylamido-4-cyanophenylboronic acid, 3-acrylamido-5-cyanophenylboronic acid, 3-acrylamido-5-nitrophenylboronic acid, 2-acrylamidomethylphenylboronic acid, 2-acrylamidomethyl-4-fluorophenylboronic acid, 2-acrylamidomethyl-5-fluorophenylboronic acid, 2-acrylamidomethyl-5-nitrophenylboronic acid, 3-acrylamidomethylphenylboronic acid, 4-acrylamidomethylphenylboronic acid, 5-acrylamidomethyl-2-fluorophenylboronic acid, 3-vinylphenylboronic acid, 4-vinylphenylboronic acid, 2-vinylphenylboronic acid, trans-2-phenylvinylboronic acid, 1-phenylvinylboronic acid, trans-2-(4-methoxylphenyl)vinylboronic acid, and boronic acid-containing monomer compatible with forming a glucose sensor. Varying or combining the selection of boronic acid moieties for the sensors can enhance the sensor performance. In various embodiments, (a) increasing the length between the boronic acid and hydrogel backbone can decreases sensitivity; (b) boronic acid with electron withdrawing groups can provide higher sensitivity than boronic acid with electron donating groups; (c) the position of boronic acid on a phenyl ring can affect the sensitivity, with a sequence of meta position>para position>ortho position providing increased sensitivity; and (d) decreasing the pKa of the boronic acid can increase the response rate.

The volume resetting agent can be polyvinyl alcohol (PVA). In other embodiments, the volume resetting agent can be one or a mixture of polymers that interact with boronic acid moieties, including but not limited to polymers containing 1,2-diols, polymers containing 1,3-diols, polymers containing alpha hydroxyl acids, copolymers containing one or a mixture of 1,2-diols, 1,3-diols and alpha hydroxyl acids, or other polymers that reversibly (e.g., ionically) interact with boronic acid moieties.

The hydrogel sensor material can further include a cofunctionality or response kinetics modifying agent. In certain specific embodiments, the response kinetics modifying agent can be N,N-dimethylethylenediamine. The molar ratio of PBA moieties to the response kinetics modifying agent can be about 1:5 to about 1:100. Suitable ratios include about 1:5, about 1:10, about 1:20, about 1:30, about 1:50, about 1:60, about 1:75, or about 1:100.

The hydrogel sensor material can be sensitive (i.e., can form reversible ionic bonds) to glucose at glucose concentrations from about 0.1 mM to about 50 mM.

The hydrogel sensor material can react to changes in the concentration of glucose within about 5 minutes by altering its volume in relation to and often proportionally to the change in glucose concentration.

The hydrogel sensor material can react to changes in the concentration of glucose with little or no hysteresis. The response of the hydrogel sensor material to glucose can be linear or substantially linear with $R^2>0.8$, $R^2>0.9$, or $R^2>0.98$.

The hydrogel sensor material can contain a uniform ordered array of particles (e.g., microparticles or nanoparticles) causing the material to diffract light; wherein
  a) reflected wavelengths of the diffracted light can directly correlate to the spacing of the particles;
  b) the particle spacing varies with changes in sensor volume so that i) an increase in volume increases particle spacing uniformly causing a red shift in the reflected light, and ii) a decrease in volume decreases particle spacing uniformly, causing a blue shift in reflected light; and
  c) the shift is related (proportional, in some embodiments) to the concentration of the analyte or group of analytes in a mixture or solution in contact with the hydrogel sensor material.

For example, the sensor material can be a photonic crystal capable of volume change that diffracts light, wherein the diffracted light has a longer wavelength when the sensor material increases in volume and has a shorter wavelength when the sensor material decreases in volume. The photonic crystal can be a polymerized crystalline colloidal array (PCCA). The photonic crystal can be holographically defined, or it can be an inverse opal.

The particles can be uniformly-sized polystyrene particles having like surface charges. In some embodiments, the particles can have a generally uniform diameter of about 50 nanometers to about 2 microns, 50 nanometers to about 300 nanometers, about 80 nanometers to about 200 nanometers, or 100 nanometers to about 200 nanometers. In certain specific embodiments, the particles have an approximate diameter of about 125-175 nm, or about 150 nanometers.

The hydrogel sensor material can include a holographic pattern causing the material to diffract light; wherein
  a) the reflected wavelength is related to the holographic pattern;
  b) the holographic pattern varies with changes in sensor volume so that i) an increase in volume causes a red shift in the reflected light, and ii) a decrease in volume causes a blue shift in reflected light; and
  c) the shift is related (proportional, in some embodiments) to the concentration of the analyte or group of analytes in a mixture or solution in contact with the hydrogel sensor material.

The invention also provides a polymer sensor comprising polymer chains that are pulled closely together by constructed crosslinks of at least two different moieties, each attached to a different polymer chain; wherein the volume of the polymer sensor can change in response to the presence of an analyte or group of analytes; the bond between the two moieties spontaneously and reversibly breaks or forms in response to changing concentrations of an analyte or group of analytes of interest in solution; and wherein:
  i) the sensor volume increases due to elastic expansion manifest from the breaking of bonds as the concentration of an analyte or group of analytes increases, and
  ii) the sensor volume decreases due to contraction against an elastic expansion force manifest from the forming of bonds as the concentration of an analyte or group of analytes decreases. The volume increase or decrease can be linear with $R^2>0.9$ or $R^2>0.98$.

The hydrogel sensor material can be combined with a means for measuring volume change, wherein the means for measuring volume change relates volume change to concentration of an analyte or group of analytes. One method to measure volume change is to embed a photonic crystal or diffraction grating (i.e., an ordered array of charged particles) in the hydrogel. A PCCA hydrogel can provide an optical readout of its volume change. The optical response can be measured using a photodiode array spectrometer. The sensor can be calibrated using this photodiode array spectrometer and two or more solutions of known glucose concentration.

The hydrogel sensor material can also be combined with a fiber optic, a white light source, and spectrometer configured to measure a reflected spectrum from the sensor material immersed in a solution containing an analyte or group of analytes of interest, the spectrum representative of sensor volume and thus representative of the concentration of an analyte or group of analytes in the solution.

The invention further provides a method of making an acrylamide hydrogel glucose sensor material that responds to an analyte in solution by changing volume while immersed in the solution in response to the presence of the analyte. The analyte can be a saccharide, a diol, a triol, a tetraol, or lactate. The method can include:
  a. synthesizing a sensor material by mixing a solution that includes an acrylamide, a bis-acrylamide, and an initiator in suitable and effective proportions with a water-based colloid that contains colloidal nanoparticles;
  b. exposing the solution to an energy source compatible with the initiator to polymerize the solution;
  c. placing the polymerized material in a hydrolyzing solution for a period of time sufficient to hydrolyze amide moieties of the material to carboxylate moieties;
  d. removing the material from the hydrolyzing solution and washing the material in water or a saltwater solution;
  e. placing the hydrolyzed material in a boronating solution to attach boronic acid moieties to the polymer chains of the material to form a boronated hydrogel, and
  f. combining the boronated hydrogel with a polyvinyl alcohol (PVA) solution so that hydroxyl moieties of the PVA form covalent bonds with boronic acid moieties of the boronated hydrogel to form crosslinks in the hydrogel, thereby shrinking the volume of the hydrogel.

In one embodiment, the sensor material of step (a) can also be combined with a water-based colloid that contains colloidal particles, followed by allowing the colloidal particles to self-organize into an ordered array.

Thus, the invention provides an analyte measurement system comprising the sensor material described herein, in combination with a fiber optic, a light source, and a device capable of measuring the color of light. The analyte measurement system can include a means to correct pH and/or ionic strength dependent measurement variations using simultaneous or near simultaneous measurements from a pH and/or ionic strength sensor. The pH and/or ionic sensor can include a material that undergoes volume change as pH and/or ionic strength varies. The sensor can be attached to the tip of a fiber optic, the sensor being in optical communication with a device capable of measuring the color of light. The sensor, which can be a polymerized crystalline colloidal array, an inverse opal, a holographically defined photonic crystal, or other material having a volume variable "optically diffracting element", can diffract light when irradiated by light. The sensor material can contain a material that absorbs white light or broad bands of light. The sensor material that absorbs white light can be lamp black.

The sensor material can respond (i.e., form or break crosslinks resulting on a change in volume) to glucose over a range of at least 0.01-5 mM glucose. The sensor material can also respond to glucose over a range of at least 0.01-10 mM glucose, at least 0.01-30 mM glucose, at least 0.01-40 mM glucose, or at least 0.01-50 mM glucose.

In other embodiments, sensor material can respond (i.e., form or break crosslinks resulting on a change in volume) to lactate over a range of at least 0.01-1 mM lactate. The sensor material can also respond to lactate over a range of at least 0.01-2 mM lactate, at least 0.01-3 mM lactate, at least 0.01-5 mM lactate, at least 0.01-10 mM lactate, or at least 0.01-20 mM lactate.

The sensor material can have a thickness of about 0.5 micrometers to 5 millimeters. In some embodiments, the thickness of the sensor material can be about 1 micrometer to about 5 millimeters, about 1 micrometer to about 1 millimeter, about 1 micrometer to about 100 micrometers, about 1 micrometer to about 50 micrometers, about 20 micrometers to about 40 micrometers, or about 30 micrometers. The thickness of the sensor material can be controlled by pressing a flat surface onto the monomer mixture on a substrate when preparing the sensor material.

Various embodiments for sensing glucose are described above, for example, where the polymer of the molecular recognition agent is a modified polyacrylamide that includes boronic acid moieties that specifically react with monosaccharides such as glucose. These sensors having boronic acid moieties can also specifically react with fructose, disaccharides, diol-containing molecules such as dopamine and various dyes (e.g., Alizarin Red), lactate, hydrofluoric acid, and anions such as fluoride ions, chloride ions, and cyanide ions, to provide a linear or near-linear change in volume.

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more components can refer to one to about ten, one to about five, or one to four, one to three, one or two, or five or more, or ten or more, depending on the context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for ranges, substituents, and components of embodiments, are for illustration only; they do not exclude other defined values or other values within defined ranges for elements modified by numerical values.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to for detection, an amount sufficient to detect an analyte, or an amount sufficient to bring about a recited effect. Determination of an effective amount is well within the capacity of persons skilled in the art based on the disclosure presented herein. The term "effective amount" is intended to include an amount of a compound or composition described herein, or an amount of a combination of compounds or compositions described herein. Thus, an "effective amount" generally means an amount that provides the desired effect.

A "polymerized crystalline colloidal array" (PCCA) is a material with an embedded ordered array of uniform colloidal particles with like surface charges, which acts as a signal transducer. Photonic crystals can include two or three-dimensional opal structures self-assembled using polystyrene or silica colloids. Photonic crystals can also consist of one, two or three-dimensional structures with characteristic dimensions on the order of the wavelength of light generated by multilayer or lithographic processes. PBA-Tris modified PCCA denotes PCCA that contains phenylboronic acid (PBA) and tris(hydroxymethyl)aminomethane (Tris). PBA-Tris-PVA modified PCCA denotes the PCCA that contains PBA, Tris, and poly(vinyl alcohol) (PVA).

Photonic crystal can be inverse opals. Inverses opals are structures with periodic porosity created from infiltrating a three-dimensional template assembled by colloidal particles with selected materials such as poly(2-hydroxyethyl methacrylate), polyacrylamide, poly(acrylic acid), poly(vinyl alcohol), poly(N-isopropylacrylamide), poly(ethylene glycol), copolymers thereof, and the like, followed by removing the template. The periodic pores are interconnected, which can facilitate diffusion, and the periodic pores can thereby provide an optical readout.

As used herein, a "gel-based sensor material" refers to a hydrogel or an organogel that can be used to as a sensor to determine the concentration or change in concentration of an analyte, wherein the sensor volume expands upon initial contact with the analyte.

A "hydrogel sensor material" is a hydrogel that includes a molecular recognition agent and a linking agent that can form reversible crosslinks, wherein 50% or more of the solvent system of the gel by volume is water.

An "organogel sensor material" is an organogel that includes a molecular recognition agent and a linking agent that can form reversible crosslinks, wherein less than 50% of the solvent system of the gel by volume is water.

A "molecular recognition agent" refers to a molecule that is reactive to an analyte. For a glucose sensor, the molecular recognition agent can be, for example, a polymer having boronic acid moieties periodically dispersed along the polymer chain. A suitable and effective molecular recognition agent can have at least about 0.1%, and/or up to 100%, of its pendant groups (e.g., hydroxyl-containing pendant groups) converted to boronic acid moieties. Typically, about 5-10%, or about 8%, of the pendant groups are converted to boronic acid moieties.

A "volume resetting agent" refers to a linking agent that can form reversible ionic crosslinks with boronic acid moieties, for example, on a molecular recognition agent. For a glucose sensor, the volume resetting agent can be poly(vinyl alcohol) (PVA).

"Reversible crosslinks" are ionic bonds formed between the molecular recognition agent and volume resetting agent (linking agent), the density of which varies by the analyte concentration.

The phrase "near linear function" refers to a correlation coefficient above about 0.8.

The phrase "tight glycemic control" or "TGC" refers to maintaining a range of blood glucose within the normal range of about 80 to about 110 mg/dL (about 4.4 to about 6.1 mM).

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Hydrogel Sensor Materials Synthesis and Glucose Sensing Measurements

A. Synthesis of Hydrogel Sensor Materials.

Highly charged monodispersed polystyrene colloids were prepared via emulsion polymerization and purified by dialysis against Millipore water (Zhang et al., *Chem. Mater.* 2013, 25, 3239). The monomers (an acrylamide and N,N'-methylenebisacrylamide mixture), aqueous polystyrene colloidal suspension, photoinitiator solution and ion exchange resin were mixed. The solution for polymerization was taken using a syringe connected with a needle that blocks the ion exchange resin. The solution was placed in a cell composed of an acrylate functionalized bottom glass slide, a 30 micrometer thick spacer, and a fluorinated top glass slide and polymerized under a mercury UV lamp. The resulting polyacrylamide hydrogel PCCA was attached to the acrylate functionalized bottom slide.

Hydrolysis was performed in an aqueous solution containing sodium hydroxide, sodium chloride, and N,N,N',N'-tetramethylethylenediamine at room temperature for a selected period of time. The PBA (e.g., 3APBA) and cofunctionality (e.g., Tris) with a desired and suitable feed ratio (e.g., about 1:10, about 1:15, about 1:16.75, about 1:20, about 1:30, about 1:60, in molar ratio) were coupled to the hydrolyzed sample in the presence of N-(3-dimethylaminopropyl)-N'-ethylcarbodiimide hydrochloride (EDC). The resulting PBA-modified hydrogel was immersed in an aqueous solution containing PVA and EDC. The hydrogel sensor materials were rinsed with 150 mM sodium chloride solution and pH 7.4 phosphate buffered glucose solution before testing to remove loosely bonded PVA. The detailed synthetic procedures for sensor materials are described further below.

B. Glucose Sensing Measurements.

Reflectance spectra were recorded in the normal direction on an inverted microscope (10× Objective, Axiovert 135, Carl Zeiss Inc.) equipped with a halogen light source, an optical fiber and a silicon photo-diode array spectrometer (292-1056 nm). A reservoir (~18 mL) was glued to the substrate where the sensor material was attached. The reservoir holds a sufficient quantity of glucose solution, such that throughout a sensing measurement, the glucose concentration change by the binding between PBA and glucose in the reservoir is negligible. The temperature of the solution above the sensor material was maintained at 37° C. using a thermocouple and heating tape. The spectrum at zero glucose concentration was measured in pH 7.4 phosphate buffer. During the sensing measurement, the blank buffer solution was removed from the reservoir and a pH 7.4 phosphate buffered glucose solution with a selected concentration was gently poured into the reservoir. After this measurement, the glucose solution was removed and another selected glucose solution was introduced to the reservoir. By applying such abrupt concentration changes inside the reservoir, a full picture of the response kinetics of the sensor material at a selected glucose concentration can be obtained upon exposure to this concentration. The stability test was performed in a warm room (constant temperature of 37° C.) where the spectra were obtained using an Ocean Optics USB 2000 spectrometer. During all measurements, no agitation was applied to the glucose solutions.

Materials and Supplies.

An acrylamide and N,N'-methylenebisacrylamide mixture (AA/BisAA mixture, 37:1 weight ratio), mixed bed resin, N,N,N',N'-tetramethylethylenediamine (99%), sodium hydroxide (97%), 3-aminophenylboronic acid hemisulfate salt (3APBA, ≥95%), tris(hydroxymethyl)aminomethane (Tris, ≥99.8%), N,N-dimethylethylenediamine (≥98.0%), N-(3-dimethylaminopropyl)-N'-ethylcarbodiimide hydrochloride (EDC, crystalline), poly(vinyl alcohol) (PVA, $M_w$ 31,000-50,000, 98-99% hydrolyzed), poly(acrylic acid, sodium salt) solution (average $M_w$~15,000, 35 wt % in $H_2O$), D(+)-glucose, phosphate buffered saline tablets and mixed bed resin (for molecular biology, BioReagent) were purchased from Sigma-Aldrich. 2,2-Diethoxyacetophenone (DEAP, 98%) was purchased from Alfa Aesar. 5-Amino-2-fluorophenylboronic acid (5A2FPBA, 98%) was purchased from Asymchem. The 30 micrometer spacer was generously provided by Nitto Denko Corporation.

Volume Response of PBA-Modified Hydrogels as a Function of Glucose Concentration.

For conventional PBA-modified hydrogels (FIG. 2a), as glucose concentration increases from 0 mM, 2:1 PBA-glucose complexes are mostly formed leading to the shrinkage of the hydrogel. During the glucose induced shrinkage, 1:1 PBA-glucose complexes can also form, in particular at higher glucose concentrations, and the combination of all these effects makes the shrinkage non-linear. When the glucose concentration exceeds the critical concentration indicated by the arrow in FIG. 2a, the swelling effect of the 1:1 complexes and the general reduction in the density of 2:1 complexes result in swelling of the hydrogel volume. After treating the conventional PBA-modified hydrogels with PVA, a volume resetting agent, the hydrogel volume shrinks at 0 mM glucose. Thus, when the PBA-PVA-modified hydrogels are exposed to clinical glucose concentrations, the formation of 1:1 complexes dominates the response, leading to a linear expansion of the hydrogel volume (FIG. 2b).

Pre-Cycling Performance of the Sensor Material in FIG. 5a-c.

This sensor material was pre-cycled (FIG. 4) and then stored in pH 7.4 phosphate buffer with physiological salinity for ~24 hours before the cyclic sweep in FIG. 5a-c was performed.

Detailed Synthetic Procedures.

1.1. Polyacrylamide PCCA (FIG. 1b Step i).

AA/BisAA mixture (0.35 g) was dissolved in a polystyrene colloidal suspension (5.0 g) and Vortex shaken for 15 minutes with a mixed bed resin. 0.1 g of DEAP solution (0.1 g DEAP dissolved in 1.0 g DMSO) as the photo-initiator was added to the above mixture and shaken for another 15 minutes. The resulting polymerization solution showed bright opalescence. The solution with ion exchange resin removed was polymerized inside a cell composed of an acrylate-functionalized bottom glass slide, a 30 micrometer thick spacer (20 mm inner diameter), and a fluoro-functionalized top slide for 2 hours under a mercury UV lamp. The resulting polyacrylamide PCCA was attached to the acrylate-functionalized bottom slide and stored in water prior to use.

1.2. Partial Hydrolysis of Polyacrylamide PCCA (FIG. 1b Step ii).

The polyacrylamide PCCA in Section 1.1 was hydrolyzed in a basic solution containing sodium hydroxide (0.16 g), sodium chloride (0.35 g), N,N,N',N'-tetramethylethylenediamine (4 g) and water (40 g) for 9 hours at room temperature. No agitation was applied during the hydrolysis.

1.3. Sensor Material in FIG. 5a-d.

The hydrolyzed PCCA in Section 1.2 was immersed in an aqueous solution containing EDC (76.6 mg), 3APBA (1.2 mg, 6.7 μmol), Tris (49.0 mg, 0.4 mmol), sodium chloride (0.1756 g), and water (20.0 g) for 24 hours at pH 4.5. To accurately weigh 3APBA, 0.124 g of 3APBA was dissolved in 40 g of Millipore water and 0.40 g of the solution was used. Tris was also first dissolved in Millipore water and the quantity of the solution that contains 49.0 mg of Tris was added. Millipore water was finally added to make the total water content 20.0 g. The same means of weighing reactants was used in the following experiments. The resulting 3APBA-Tris PCCA was treated with PVA aqueous solution (20 g, 1.25 wt %) in the presence of EDC (0.15 g) for 24 hours.

1.4. Sensor Material in FIG. 5e-f.

The hydrolyzed PCCA in Section 1.2 was immersed in an aqueous solution containing EDC (76.6 mg), 3APBA (2.2 mg, 13.3 μmol), Tris (49.0 mg, 0.4 mmol), sodium chloride (0.1756 g), and water (20.0 g) for 24 hours at pH 4.5. The resulting 3APBA-Tris PCCA was treated with PVA aqueous solution (20 g, 1.25 wt %) in the presence of EDC (0.15 g) for 24 hours.

1.5. Sensor Material in FIG. 7a-b.

The hydrolyzed PCCA in Section 1.2 was immersed in an aqueous solution containing EDC (76.6 mg), 5A2FPBA (1.9 mg, 13.3 μmol), Tris (49.0 mg, 0.4 mmol), sodium chloride (0.1756 g), dimethyl sulfoxide (3.0 g) and water (17.0 g) for 24 hours at pH 4.5. The resulting 5A2FPBA-Tris PCCA was treated with PVA aqueous solution (20 g, 1.25 wt %) in the presence of EDC (0.15 g) for 24 hours.

1.6. Sensor Material in FIG. 7c-d.

The hydrolyzed PCCA in Section 1.2 was immersed in an aqueous solution containing EDC (76.6 mg), 3APBA (3.0 mg, 16.0 μmol), N,N-dimethylethylenediamine (35.3 mg, 0.4 mmol), sodium chloride (0.1756 g), and water (20.0 g) for 24 hours at pH 4.5. The resulting 3APBA-N,N-dimethylethylenediamine PCCA was treated with PVA aqueous solution (20 g, 1.25 wt %) in the presence of EDC (0.15 g) for 24 hours.

1.7. Sensor Material in FIG. 8 (Inverse Sensor Design).

The polyacrylamide hydrogel was hydrolyzed for 16 hours using the solution in Section 1.2 and then treated with a solution containing EDC (76.6 mg), Tris (49.0 mg), sodium chloride (0.1756 g) and water (20.0 g) at pH 4.5. The resulting PCCA is denoted as Tris PCCA. Polyacrylic acid partially modified with 3APBA was used as the volume resetting agent. The sodium salt form of polyacrylic acid (0.846 g of 35 wt % aqueous solution) was coupled with 3APBA (74.4 mg) in the presence of EDC (76.6 mg) at pH 4.5. The Tris PCCA was then treated with the partially modified polyacrylic acid solution at pH 7.0.

1.8. Chemical Structure of PBA-Tris-PVA PCCA.

A detailed chemical structure of the reversible crosslinks in the PBA-Tris-PVA PCCA hydrogel matrix is shown in FIG. 3. The hydrogel backbone primarily contains five types of linear repeating units: amide, Tris, PBA, carboxylic acid and ester. The total concentration of Tris and PBA functionalities in the hydrogel is controlled by parameters in the hydrolysis process (FIG. 1b step ii). Because the chemical contents of the hydrolysis solution and the temperature of the hydrolysis reaction are fixed in this study, the total concentration of Tris and PBA functionalities is only determined by the hydrolysis time (the quantity of the hydrolysis solution is far in excess relative to the hydrogel sensor material).

The molar ratio of PBA to Tris functionality inside the hydrogel matrix is controlled by the feed ratio during functionalization after hydrolysis (FIG. 1b step iii, the total quantity of Tris and PBA is fixed to be in great excess to the carboxylates created during hydrolysis). A portion of the leftover carboxylates are crosslinked with hydroxyls of PVA in the presence of EDC (Everaerts et al., *J. Biomed. Mat. Res. Part A* 2008, 85A, 547). However, the concentration of the resulting ester linkages cannot be quantitatively determined Raman spectroscopy was performed on dry hydrogel thin films without embedded polystyrene colloids.

Figure 9:
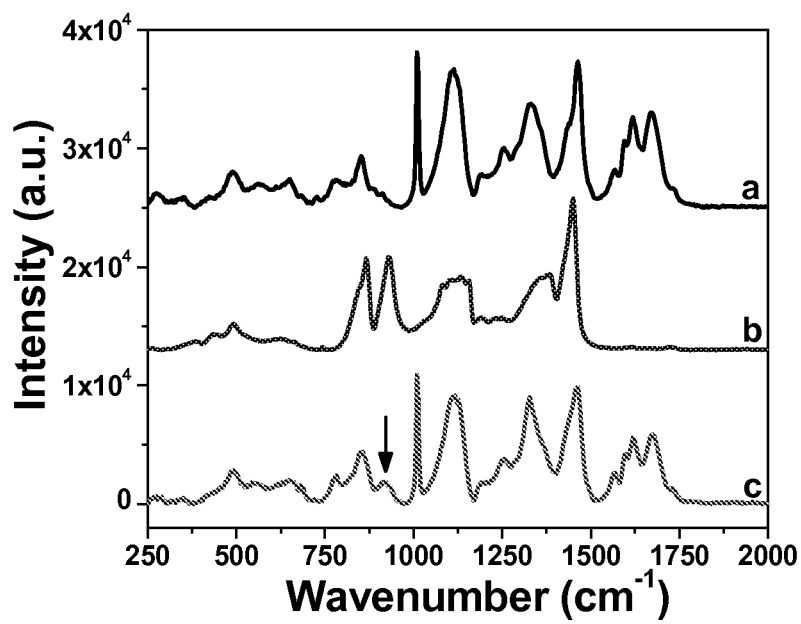
FIG. 9. Raman spectroscopy spectra of (a) 3APBA-Tris-modified polyacrylamide film, (b) PVA film, and (c) 3APBA-Tris-PVA-modified polyacrylamide film.

Two pieces of 30 μm thick polyacrylamide hydrogel films were hydrolyzed for 9 hours followed by functionalization with 3APBA and Tris (molar feed ratio 1:30) in the presence of EDC. The Tris-3APBA-modified hydrogel film was rinsed multiple times with Millipore water and dried in air for Raman spectroscopy (FIG. 9a). The other Tris-3APBA-modified hydrogel film was treated with PVA in the presence of EDC for 24 hours, rinsed extensively with Millipore water, dried in air and measured with Raman spectroscopy (FIG. 9c). The peak at 917 cm$^{-1}$ indicated by the arrow in FIG. 9c is ascribed to C—C stretching in PVA (c.f., FIG. 9b), indicating the immobilization of PVA in the Tris-3APBA-modified hydrogel.

1.9. Inductively Coupled Plasma Analysis (ICP).

ICP analysis on the boron concentration of bulk hydrogel samples was performed on a PerkinElmer 2000DV ICP-OES. The bulk hydrogel samples used for ICP analysis do not have embedded polystyrene colloids. Polyacrylamide hydrogel with the same composition as the polyacrylamide PCCA matrix in FIG. 1b was used as the starting material for ICP sample preparation. The detailed preparation procedures are summarized in Table 1.

TABLE 1

Sample preparation for ICP analysis on boron concentration.

| Sample label [a] | A | B | C | D |
|---|---|---|---|---|
| Hydrolysis time [b] | 9 h | 9 h | 9 h | 9 h |
| Functionalization [c] | 3APBA | 3APBA | 3APBA:Tris | 3APBA:Tris |
| PVA infiltration [d] | No | Yes | No | Yes |
| Freeze drying | Yes | Yes | Yes | Yes |

[a] The starting material of sample A-D is bulk polyacrylamide hydrogel (2.5 g) containing about 0.17 g polyacrylamide.
[b] The hydrolysis solution for each sample comprises sodium hydroxide (0.40 g), sodium chloride (0.88 g), N,N,N',N '-tetramethylethylenediamine (4.0 g) and water (100 g). The hydrolysis solution after 4.5 hours was replaced with fresh hydrolysis solution. The hydrolysis was conducted at room temperature.
[c] Functionalization was performed in the presence of EDC as the coupling agent at pH 4.5. The quantity of EDC and functionality was in excess relative to the carboxylates created during hydrolysis. The feed ratio of 3APBA:Tris during functionalizing Sample C and D was 1:30.
[d] After 24 hours of PVA infiltration in the presence of EDC, sample B and D were rinsed with Millipore water for 24 hours before freeze drying. Sample A and B, which were not infiltrated with PVA, were rinsed with Millipore water for 24 hours before freeze drying. Rinsing included multiple exchanges of Millipore water.

The boronic acid contents in Sample A-D are summarized in Table 2. The PVA concentration in Sample B and D can be calculated using the calibrated boronic acid content in Sample A-B and C-D, respectively (Equation 1).

$$w = \frac{C_{without\ PVA} - C_{with\ PVA}}{C_{without\ PVA}} \times 100\%$$  Equation 1

Here w denotes the PVA weight percentage in the PVA infiltrated hydrogels. $C_{without\ PVA}$ and $C_{with\ PVA}$ denote the calibrated boronic acid content in hydrogel samples before and after PVA infiltration. The 3APBA-Tris-PVA modified hydrogel (Sample D) contains a high PVA concentration (27 wt %), about twice the PVA concentration in the 3APBA-PVA modified hydrogel (Sample B, 13 wt %), even the 3APBA concentration is much lower than in Sample B. This indicates that the Tris functionality is also a major contributor to immobilizing PVA in the hydrogel in addition to boronic acids.

TABLE 2

Boron concentrations by ICP in Sample A-D.

| Sample | A | B | C | D |
|---|---|---|---|---|
| Functionality | 3APBA | 3APBA-PVA | 3APBA-Tris | 3APBA-Tris-PVA |
| Boron concentration [a] | 0.90% | 0.76% | 0.11% | 0.08% |
| Boronic acid content [b] | 0.83 | 0.70 | 0.10 | 0.07 |
| (Dry mass)/(mass after freeze drying) [c] | 0.92 | 0.90 | 0.95 | 0.90 |
| Calibrated boronic acid content [d] | 0.90 | 0.78 | 0.11 | 0.08 |
| PVA concentration [e] | NA | 13% | NA | 27% |

[a] Boron weight percentage in the freeze-dried hydrogels.
[b] mmole of 3APBA per gram of freeze-dried hydrogel.
[c] The concentration of bound water in freeze-dried hydrogels were determined by thermogravimetric analysis. The "dry mass" is the mass after removing the bounded water at 120° C. The ratio of "dry mass" to "mass after freeze drying" was used to calibrate the "boronic acid content" calculated from the ICP results.
[d] mmole of 3APBA per gram of dry hydrogel with bound water removed as described in c.
[e] PVA weight percentage in the hydrogels.

1.10. Response Kinetics of the Hydrogel Sensor Material.

We observed two interesting kinetic phenomena during the cyclic sweep of glucose concentration (FIG. 5c). First, for any given glucose concentration step (increasing or decreasing), the response time is faster upon decreasing glucose concentration than increasing glucose concentration. Second, the response time is faster for increasing glucose concentration at low glucose concentrations, and faster at decreasing glucose concentrations at high glucose concentrations. We have confirmed the diffusion of glucose inside the hydrogel does not dominate the kinetics. The response times of the 30 µm thick hydrogels described herein, and a thinner (10 µm) or thicker (50 µm) hydrogel are similar. Only when the hydrogel is 120 µm thick do we observe a significant slowing of the response kinetics, presumably due to the time it takes glucose to diffuse through the thick hydrogel.

The reason that the response is faster for decreasing glucose concentration relative to increasing glucose is likely primarily due to the different concentrations of chemical components in the hydrogel. The concentration of boronic acid is ~8 mM, and the concentration of the PVA hydroxyl groups inside the hydrogel is ~600 mM (both calculated from data in Table 2). For increasing glucose concentration, the hydrogel only expands when free glucose finds a PBA-PVA complex. Given the low concentration of both free glucose and the PBA-PVA complexes, the reaction kinetics are relatively slow. For decreasing glucose concentration, the hydrogel contracts when PVA, which is present in high concentration, finds a PBA made available by a departing glucose molecule. Because the PVA has a high concentration, complex formation is rapid.

1.11. Sensor Performance without Tris Functionality.

The sensors were prepared by hydrolyzing the polyacrylamide PCCAs for 45 minutes and 70 minutes, respectively, followed by coupling with 3APBA in the presence of EDC. PVA was then incorporated into the 3APBA modified PCCAs. The sensors without Tris show significant signal drift toward longer wavelength during the cyclic test (FIGS. 6a and b). This is likely caused by the gradual loss of PVA and dislocation of PVA chains from the vicinity of immobilized boronic acids. The sensor with low 3APBA content (hydrolyzed for 45 minutes, FIG. 6a) shows less sensitivity to glucose compared with the sensor with high 3APBA content (hydrolyzed for 70 minutes, FIG. 6b).

Example 2. Synthesis of a Crystalline Colloidal Array (CCA)

Figure 11:
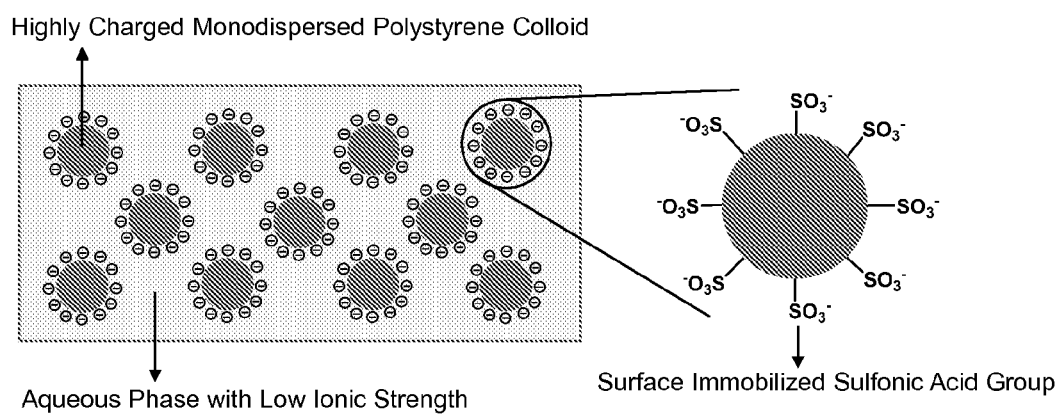
FIG. 11. A schematic illustration of a crystalline colloidal array (CCA), according to one embodiment.

Sodium bicarbonate (0.24 g) was dissolved in Millipore water (200 g) in a three-neck flask. The solution was purged by nitrogen under stirring for 40 minutes. Dihexyl sulfosuccinate sodium salt solution (2.28 g) and Millipore water (28.56 g) were added to the flask and the temperature was increased to 50° C. A monomer mixture of de-inhibited styrene (47.28 g) and divinylbenzene (4.44 g) was added to the reaction system at a rate of 4 mL/min. 3-Allyloxy-2-hydroxy-1-propanesulfonic acid sodium salt solution (15.72 g) was diluted with 12 mL Millipore water and added into the flask 1.5 hours after the monomer mixture was added. The temperature was increased to 70° C. Ammonium persulfate (0.64 g) was dissolved in Millipore water (20 mL) and added into the flask. The reaction system was refluxed for 6 hours and cooled to room temperature. The resulting polystyrene colloid suspension was purified by dialysis for 30 days until the electrical resistance of the water bath reached the same value as Millipore water. The suspension shows bright opalescence due to Bragg diffraction of visible light by the formed CCA (FIG. 11).

Example 3. Synthesis of Hydrogel Thin Films with Embedded Ordered Array of Like-Charged Polystyrene Spheres (Polyacrylamide Polymerized Crystalline Colloidal Array) (PCCA)

Acrylate functionalities were introduced to bottom glass slides by treating them with 20 mM 3-(trimethoxysilyl) propyl methacrylate in toluene overnight. Top slides were functionalized in 20 mM trichloro(1H,1H,2H,2H-perfluorooctyl)silane in chloroform overnight. Both slides were rinsed with ethanol and blown dry using nitrogen gas. The mold for polymerization consisted of a sandwich structure of a bottom slide, a spacer and a top slide. The spacer can be made of any suitable and effective material such as double-sided tape or a polymer film. An acrylamide/bis-acrylamide mixture (0.35 g) (37:1 wt. ratio), and 0.2 g mixed bed resin were added to 5 g of a polystyrene colloidal suspension. The mixture was shaken on Vortex mixer for 15 minutes. 2,2-Diethoxyacetophenone (DEAP) (0.1 g) solution (0.1 g DEAP in 1.0 g dimethyl sulfoxide) was added and the resulting polymerization solution was mixed for another 15 minutes followed by a 5 minute nitrogen purge to remove oxygen. The nitrogen bubbles trapped in the solution were removed by vacuum.

The polymerization solution was taken up by a syringe and dropped into a well consisting of a bottom slide and a spacer. The top slide was closed carefully to avoid air bubbles and reduce shear force. The sealed cell was clamped and stored in the dark to improve the quality of CCA. The polymerization solution with bright opalescence was polymerized for 2 hours using a mercury UV lamp. After polymerization, the top slide was carefully removed and the resulting PCCA (see FIG. 3) attached to the bottom slide was rinsed intensively and equilibrated in Millipore water for use.

Example 4. Chemical Modification of a Polyacrylamide Hydrogel Thin Film to Form Glucose Sensor Materials Polyacrylamide hydrogel thin films were hydrolyzed in a solution containing 0.16 g sodium hydroxide, 0.35 g sodium chloride, 4 g N,N,N',N'-tetramethylethylenediamine, and 40 g water at room temperature (~22° C.) for 9 hours. 3-Aminophenylboronic acid and tris(hydroxymethyl)aminomethane (Tris) at a 1:30 molar ratio were coupled to the hydrolyzed hydrogel in the presence of N-(3-dimethylaminopropyl)-N'-ethylcarbodiimide hydrochloride. The resulting PBA-Tris modified hydrogel was immersed in a poly(vinyl alcohol) solution containing EDC. To improve the operational stability, PBA-cofunctionality-PVA modified hydrogel was rinsed with dimethyl sulfoxide to remove water and was reacted with hexamethylene diisocyanate to form crosslinks between PVA and the hydroxyls of the immobilized Tris on the hydrogel matrix (resulting in crosslinking on about 5% or about 10% of the repeat units on the hydrogel backbone). The resulting hydrogel sensor materials were rinsed with 150 mM sodium chloride solution and pH 7.4 phosphate buffered glucose solution before testing.

Example 5. Hydrogel-Based Glucose Sensor Material

A glucose sensor was prepared based on a glucose-responsive hydrogel with a volume linearly correlated with glucose concentration (about 0.05 mM to about 50 mM) under physiological conditions (pH 7.4, physiological ionic strength, 37° C.). The thickness of the glucose responsive hydrogel can be made from nanometer to micrometer scale depending on the fabrication technique. Typically, a 30 micrometer thick polyacrylamide hydrogel is synthesized via photopolymerization followed by a hydrolysis process to create carboxylate sites for a concomitant boronation step. After boronic acid moiety functionalization, a polyol such as PVA is incorporated to the hydrogel. The volume of the final hydrogel responds to glucose linearly under physiological conditions. A photonic crystal can be added during synthesis. A polyacrylamide hydrogel containing an ordered array of particles, such as polystyrene spheres or other colloidal particles, can be used as one of the transducers to report volume changes as diffraction wavelength shifts.

The diffraction wavelength of the photonic crystal glucose sensor can be linearly shifted within a short time due to a change in the lattice spacing of the three-dimensionally ordered particles (e.g., in colloidal form) caused by the volume change of the glucose-responsive hydrogel matrix. For example, a linear red shift in diffraction wavelength with a slope of about 2 nm/mM glucose can be observed. When cycled from 0-50 mM and 50-0 mM glucose with a 10 mM step, the sensor shows almost no hysteresis or drift. The sensor shows almost no drift during storage in 5 mM glucose over a period of 3 days. These features demonstrate that the sensors described herein have linear responses to the presence of glucose, minimal hysteresis and drift, and good stability. These features also confirm that this rational design is compatible with the requirements for continuous glucose monitoring.

The invention thus provides a new chemical device that takes advantage of novel glucose responsive hydrogels. Significant features of the sensor described herein include its broad sensing range, linear and fast response, very small hysteresis and response stability under physiological environments. The linear response allows an easy calibration step, which can be a two-point calibration or even one-point calibration. The fast response kinetics enable high frequency measurements to adequately monitor the glucose concentration fluctuations in body fluids. No obvious hysteresis and response stability contribute to the accurate measurement of glucose levels over the desired working period. These features show great potential for both point-of-care glucose testing and continuous glucose monitoring in clinical settings.

FIG. 1 shows the general design and synthesis of a volume resetting agent-loaded photonic hydrogel glucose sensor material, alternatively referred to as a polymerized crystalline colloidal array (PCCA). A variable diffraction grating created by the self-organization of colloidal materials can be used as the transducer to report the volume change of a final glucose responsive hydrogel. Materials such as polystyrene, silica, or latex can be used as the colloidal materials. Various colloidal materials are commercially available from suppliers such as Life Technologies (Carlsbad, Calif.), which supplies various particles of about 20 nm to about 10 microns in diameter, including various latex particles. Colloidal material particles that have greater surface charge and that can be suspended in an ion-free aqueous environment can also be used. Such particles can be prepared by the procedures described in *Journal of Colloid and Interface Science* 232, 76-80 (2000) and *Chemistry of Materials* 25, 3239-3250 (2013). Polyacrylamide can be used as a water-soluble hydrogel material.

Figure 12:
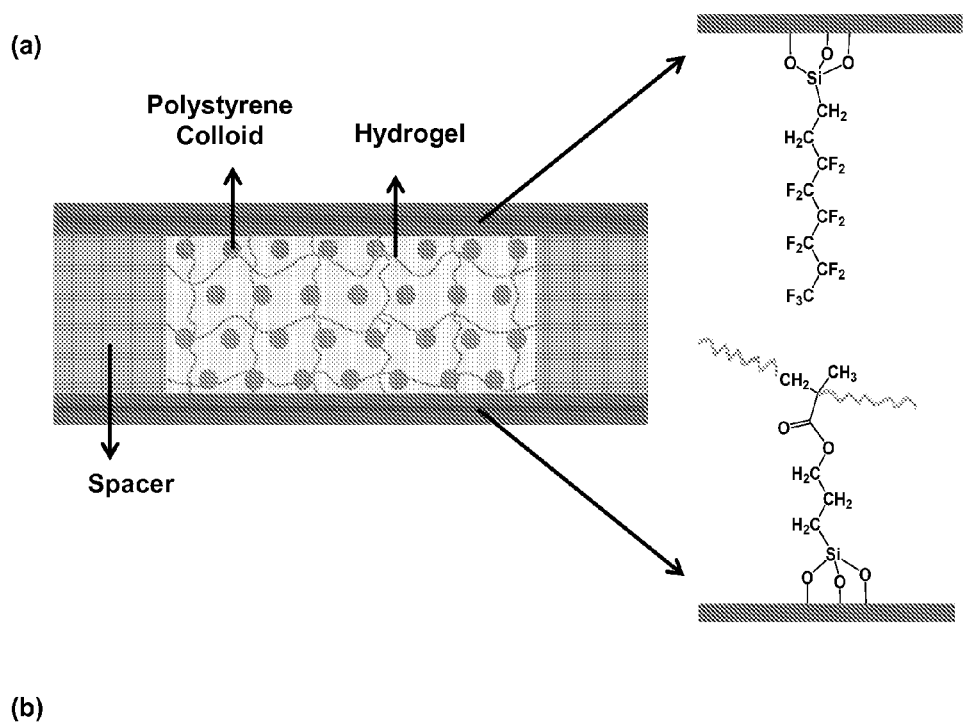
FIG. 12. (a) A schematic of a mold for fabricating photonic crystal embedded hydrogels (e.g., a PCCA) with different thicknesses; step (i) of FIG. 1b; (b) the reflection intensity of diffraction peaks of random spots on a PCCA sample.
Figure 12:
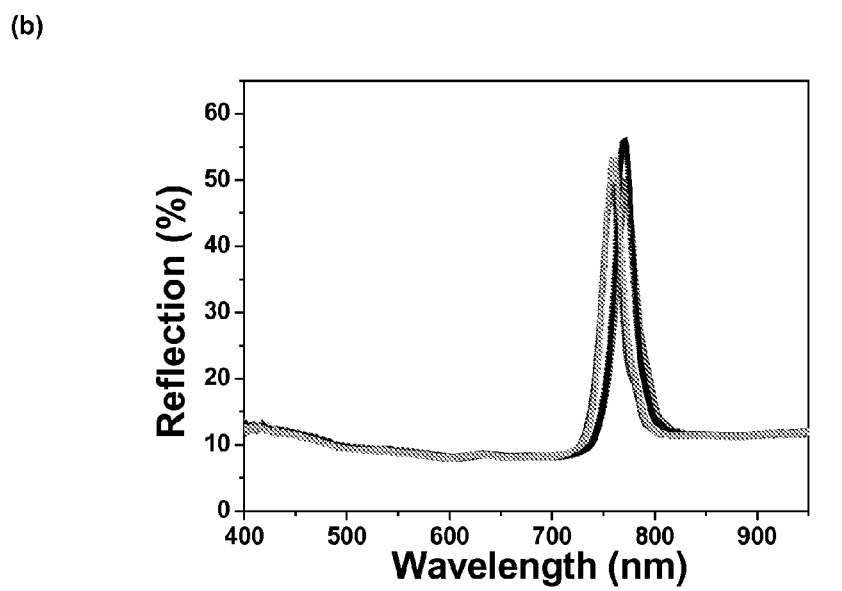

FIG. 12a shows a cell or mold for the polymerization step in FIG. 1 step (i). The cell can include a bottom glass slide typically functionalized with 3-(trimethoxy-silyl)propyl methacrylate, a top slide typically functionalized with trichloro(1H,1H,2H,2H-perfluorooctyl)silane, and a spacer in between. The hydrogel thickness is controlled by the thickness of the spacer. After polymerization, the top glass slide can be removed and the resulting hydrogel remains attached to the bottom slide. FIG. 12b shows the intensity of reflection peaks (e.g., from white light provided by a halogen light source) as measured by a spectrometer. The peak position can be directly read from a spectrometer without complicated calculation. The narrow distribution of the diffraction peaks individually measured from different regions of the PCCA indicates that the PCCA has a laterally homogeneous structure.

Figure 5:
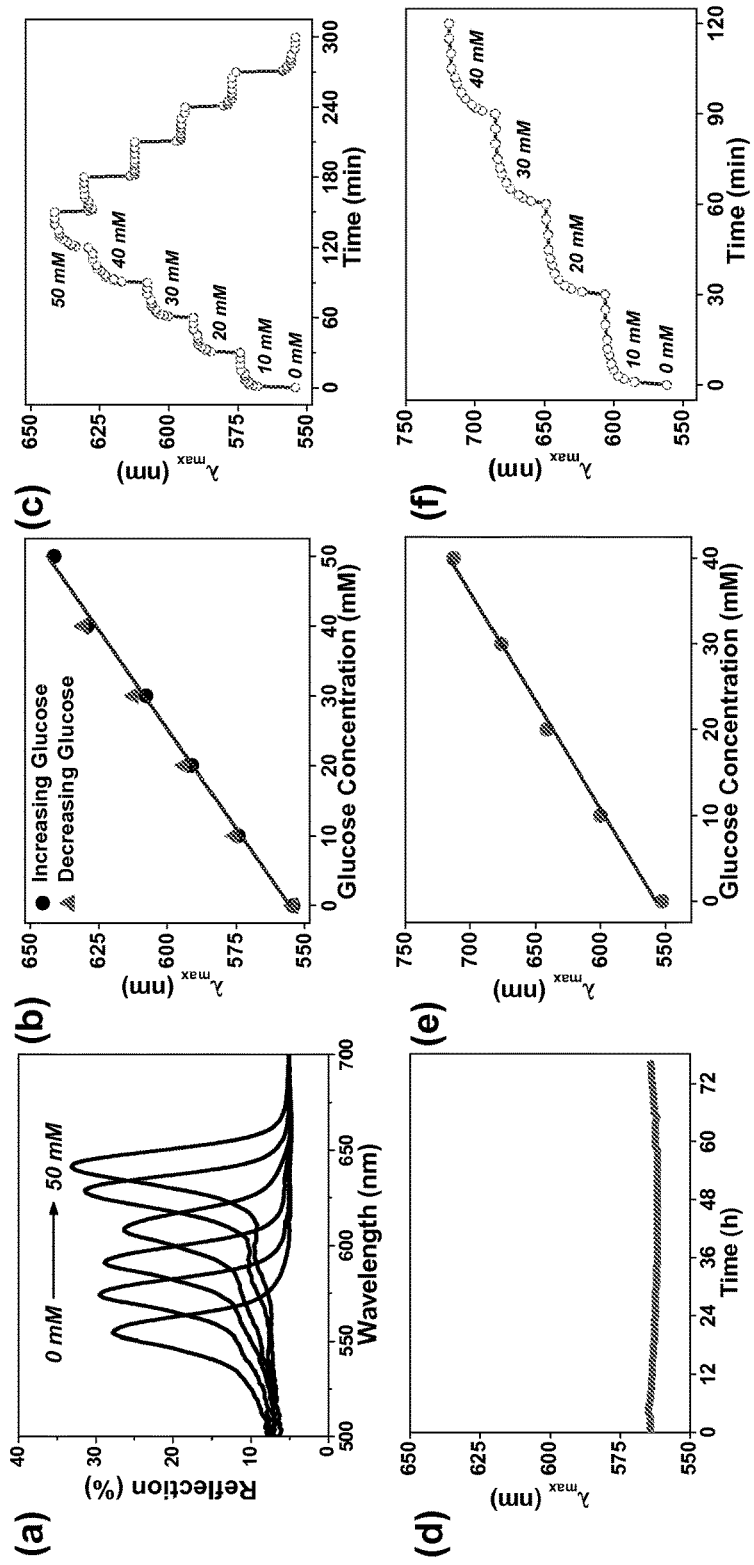
FIG. 5. Glucose sensing performance of the PBA-Tris-PVA PCCA. (a) Diffraction spectra during an increasing glucose sweep in 10 mM steps. (b) Diffracted wavelength during a cyclic sweep of glucose concentration between 0 and 50 mM glucose. (c) Temporal evolution of the diffracted wavelength during the glucose concentration sweep. (d) Diffracted wavelength over 72 hours in 5 mM glucose. (e) Diffracted wavelength as a function of glucose concentration. (f) Temporal evolution of the diffracted wavelength during the glucose concentration. Lines in (b) and (e) are linear fits. All tests were performed in pH 7.4 phosphate buffered glucose solutions at 37° C. $\lambda_{max}$ is the wavelength corresponding to the maximum of the first order diffraction peak.
Figure 6:
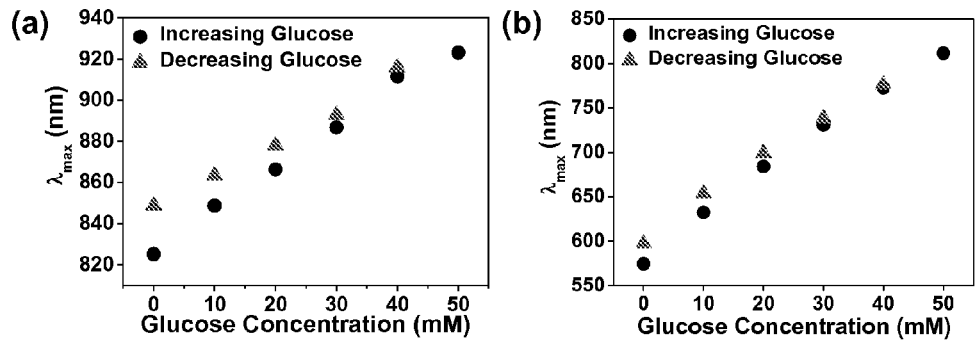
FIG. 6. Diffracted wavelength of glucose responsive PCCA containing 3APBA without Tris during a cyclic sweep of glucose. (a) Low 3APBA content; (b) high 3APBA content. The measurement was performed in pH 7.4 phosphate buffered glucose solutions at 37° C. $\lambda_{max}$ is the wavelength corresponding to the maximum of the first order diffraction peak.

FIG. 5 shows functional characteristics of a 3APBA-Tris-PBA-modified PCCA sensor during a round-way glucose titration test in pH 7.4 phosphate buffer with physiological salinity at 37° C. FIG. 5b shows the spectral response of the sensor to titration from 0-50 mM glucose and back to 0 mM glucose in 10 mM steps. The data points show high linearity ($R^2 > 0.99$) with an overall wavelength shift of ~100 nm. The wavelengths for any specific glucose concentration nearly overlap indicating almost no hysteresis or drift exists (in many samples, the hysteresis is too small to be measured). FIG. 5c shows the response kinetics in a glucose titration test. Under most glucose changes, the sensor provides ~70-90% of the wavelength shift within about 5 minutes. This titration test proves the linear, fast response, minimal hysteresis and minimal drift of the sensor in this invention.

FIG. 7a shows another sensor example with increased response magnitude and kinetics compared to FIG. 5b and FIG. 5c using a more reactive boronic acid, 5A2FBA, instead of 3APBA, providing a broader wavelength shift (180 nm) from 0-10 mM glucose. The sensor reaches equilibrium within the first 5 minutes as indicated in the kinetics curve (FIG. 7b). With the same boronic acid content in the hydrogel sensor material (e.g., about 8% of acrylamide amino groups functionalized to form 5A2FPBA), increasing the boronic acid reactivity to glucose can increase the sensitivity and response kinetics of the sensor material. The ratio of diffraction wavelength shift/glucose concentration (i.e., sensitivity) can be tuned to effectively respond to low and high glucose concentration ranges.

FIG. 5d shows the sensor stability when tested in a solution with physiological characteristics (in pH 7.4 phosphate buffer with physiological salinity at 37° C.). A static test was performed by immersing the sensor in 5 mM glucose and monitoring the diffraction wavelength. During the static test, the diffraction wavelength remained constant within a few nm (less than 2 nm) for more than 72 hours. This test with the 3APBA hydrogel material demonstrates the extraordinary stability of the sensor material in a solution with physiological characteristics.

FIGS. 13a and 13b compare the response magnitude and kinetics of 3APBA-Tris-PVA-modified PCCA in pH 7.4 phosphate buffer and pH 7.4 blood serum. The sensitivity in blood serum (7.8 nm per mM glucose) is higher than in pH 7.4 phosphate buffer (4.0 nm per mM glucose). However, the response kinetics in blood serum is slightly slower than in pH 7.4 phosphate buffer.

Figure 13:
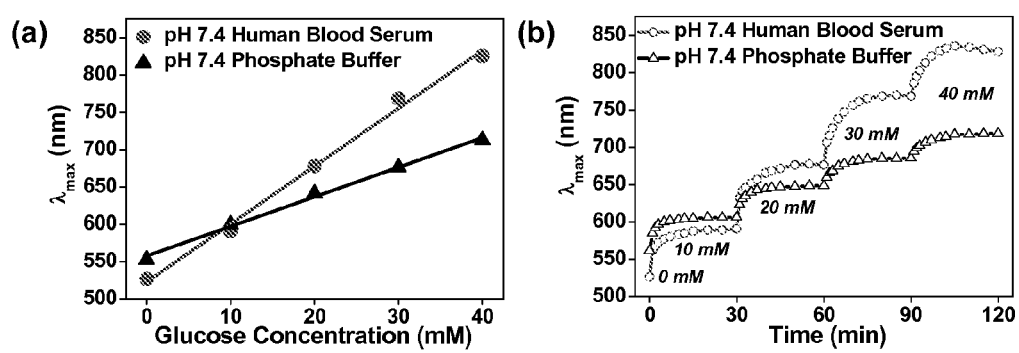
FIG. 13. 3APBA-Tris-PVA sensor performance: (a) and (b) compare (a) the response magnitude and (b) kinetics of a sensor material in pH 7.4 phosphate buffer with physiological salinity at 37° C. and pH 7.4 blood serum at 37° C.
Figure 14:
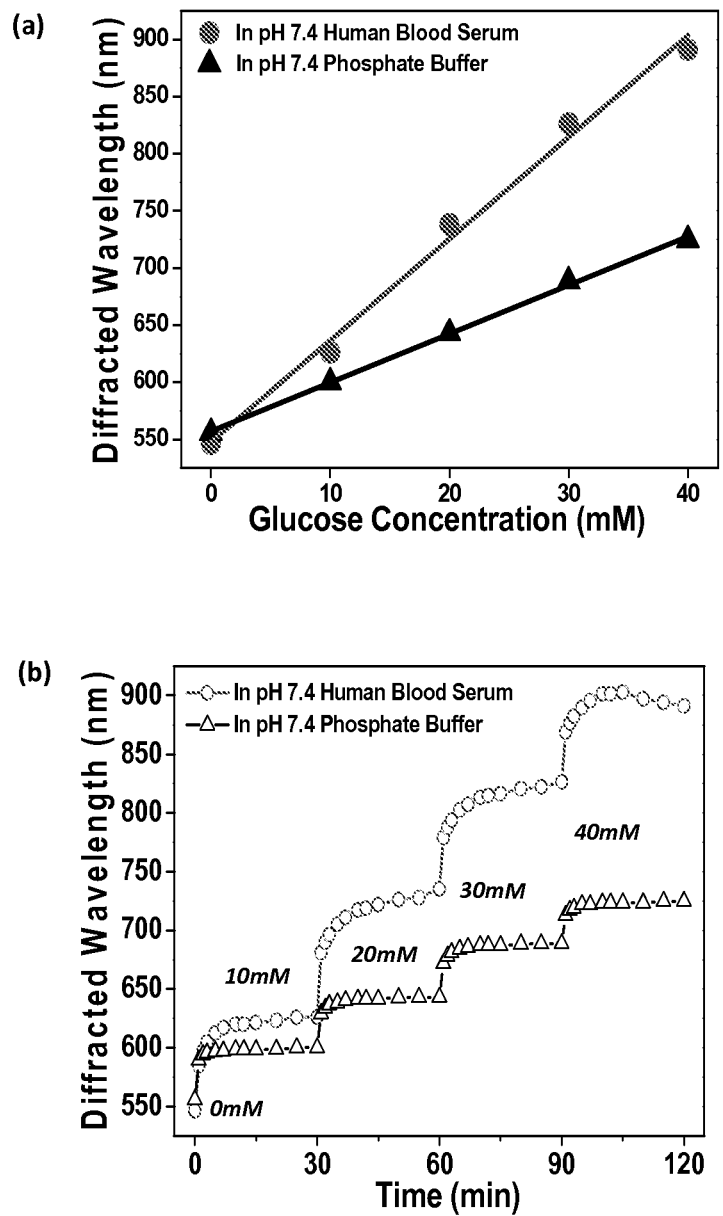
FIG. 14. The glucose responsiveness (a) and response kinetics (b) of 3APBA-N,N-dimethylethylenediamine-PVA modified PCCA in pH 7.4 phosphate buffer with physiological salinity and pH 7.4 blood serum at 37° C. The response magnitude and kinetics of sensor materials can be improved by incorporating an amine based co-functionality, here for example, N,N-dimethylethylenediamine, on the hydrogel backbone.

FIG. 14 shows the increased response magnitude and kinetics in pH 7.4 phosphate buffer with physiological salinity at 37° C., compared to FIG. 13 by using a co-functionality other than Tris, N,N-dimethylethylenediamine, which forms complexes with boronic acid to increase its reactivity to glucose.

Thus, suitable and effective glucose sensors have been prepared and evaluated. Many samples have been prepared, the fabricating process has been described, and their use has been demonstrated. Sensor performance has been fully evaluated in vitro in solutions with physiological characteristics. The sensors described herein can therefore be used for a variety of sensing operations including continuous glucose monitoring in clinical settings.

Example 6. Organogel-Based Sensor Material

Figure 15:
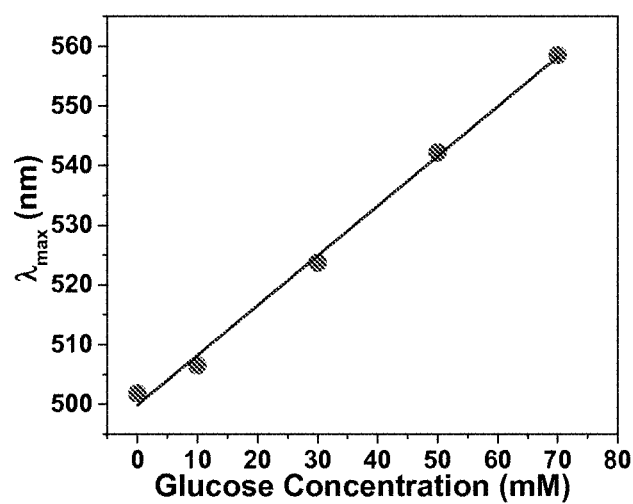
FIG. 15. Diffracted wavelength as a function of glucose concentration in DMSO/PBS mixture (3:2 volume ratio) at room temperature. The $\lambda_{max}$ is the wavelength corresponding to the maximum of the diffraction peak.

Polyacrylamide PCCA was synthesized following the procedure in Example 1. The polyacrylamide PCCA was hydrolyzed in a basic solution containing sodium hydroxide (0.16 g), sodium chloride (0.35 g), N,N,N',N'-tetramethylethylenediamine (4 g), and water (40 g) for 70 minutes at room temperature. No agitation was applied during the hydrolysis. The partially hydrolyzed polyacrylamide PCCA was placed in an aqueous solution containing EDC (76.6 mg), 3APBA (74.3 mg), sodium chloride (0.1756 g), and water (20.0 g) for 24 hours at pH 4.5. The resulting sample was treated with PVA aqueous solution (20 g, 1.25 wt %) in the presence of EDC (0.15 g) for 24 hours. The sample was then rinsed with 150 mM NaCl aqueous solution and equilibrated in a DMSO/PBS mixture (3:2 volume ratio) at room temperature. The phosphate buffer prior to mixing with DMSO had a pH of 7.4. A reservoir (~18 mL) was glued to the substrate where the sensor material was attached. The measurements were performed at room temperature. The spectra were obtained using an Ocean Optics USB 2000 spectrometer coupled with a tungsten halogen light source and optical fibers. The spectrum at zero glucose concentration was measured in a DMSO/PBS mixture. During the sensing measurements, the blank DMSO/PBS mixture was removed from the reservoir and a DMSO/PBS mixture containing 10 mM glucose was gently poured into the reservoir. After this measurement, this glucose solution was removed and another DMSO/PBS mixture containing a selected glucose concentration was introduced to the reservoir. The results of several measurements are shown in FIG. 15. A linear relationship to glucose concentration was observed. The $\lambda_{max}$ is the wavelength corresponding to the maximum of the diffraction peak.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A gel-based sensor that linearly responds to an analyte's concentration in contact with the sensor by changing volume, the sensor comprising: a crosslinked gel a volume resetting agent, and a hydrogen bond between the crosslinked gel and the volume resetting agent, wherein:
   a) the crosslinked gel comprises a molecular recognition agent that selectively and reversibly binds an analyte, and a drift-reducing agent;
   b) the volume resetting agent comprises a heteroatom functionality that reversibly bonds the molecular recognition agent; and
   c) the crosslinked gel is a hydrogel or an organogel, and the analyte binds to the molecular recognition agent in a 1:1 ratio;
   wherein an increase in the concentration of the analyte in contact with the sensor disrupts bonding between the molecular recognition agent and the heteroatom functionality as a function of the concentration to linearly increase the volume of the hydrogel or organogel, or a decrease in the concentration of the analyte in contact with the sensor reestablishes bonding between the molecular recognition agent and the heteroatom functionality as a function of the concentration to linearly decrease the volume of the hydrogel or organogel.

2. The sensor of claim 1 wherein the molecular recognition agent comprises a boronic acid, and the heteroatom functionality comprises a hydroxyl.

3. The sensor of claim 1 wherein the molecular recognition agent comprises a hydroxyl, and the heteroatom functionality comprises a boronic acid.

4. The sensor of claim 1 wherein the sensor comprises a polyacrylamide polymer.

5. The sensor of claim 1 wherein the drift-reducing agent comprises a 1,3-diol.

6. The sensor of claim 5 wherein the drift-reducing agent comprises a covalently bonded tris(hydroxymethyl)aminomethane moiety.

7. The sensor of claim 1 wherein the molecular recognition agent comprises phenylboronic acid, 3-aminophenylboronic acid, 5-amino-2-fluorophenylboronic acid, 4-amino-3-fluorophenylboronic acid, or a phenylboronic acid optionally substituted with an electron withdrawing group.

8. The sensor of claim 1 wherein the crosslinked gel comprises a covalently bonded cofunctionality compound to provide the sensor with improved response magnitude, kinetics, or improved response magnitude and kinetics, than a sensor without the cofunctionality compound.

9. The sensor of claim 1 wherein the sensor is linearly responsive to glucose concentrations from about 0.05 mM to about 50 mM.

10. The sensor of claim 8 wherein the cofunctionality compound comprises a secondary amine or tertiary amine.

11. The sensor of claim 9 wherein the sensor material responds to changes in the concentration of glucose with little or no hysteresis, and the response of the sensor material to glucose is substantially linear, wherein the substantially linear response has an $R^2$ value of about 0.85 to about 0.99.

12. The sensor of claim 1 wherein the sensor comprises a like-charged colloidal material dispersed throughout the sensor, wherein the molecular recognition agent, the volume resetting agent, the colloidal material, and a solvent form a hydrogel polymerized crystalline colloidal array (PCCA) or a organogel PCCA.

13. The sensor of claim 12 wherein the charged colloidal material forms a uniform ordered array of particles causing the material to diffract light; wherein
   a) the reflected wavelengths correlate to the spacing of the particles;
   b) the particle spacing varies with changes in sensor volume so that
      i) an increase in volume increases particle spacing uniformly causing a red shift in the reflected light, and
      ii) a decrease in volume decreases particle spacing uniformly, causing a blue shift in reflected light; and
   c) the shift is related to the concentration of the analyte or group of analytes in the solution.

14. The sensor of claim 1 further comprising a holographic pattern causing the material to diffract light; wherein
   a) the reflected wavelength is directly related to the holographic pattern;
   b) the holographic pattern varies with changes in sensor volume so that:
      i) an increase in volume causes a red shift in the reflected light, and
      ii) a decrease in volume causes a blue shift in reflected light; and
   c) the shift is proportional to the concentration of the analyte or group of analytes in the solution.

15. The sensor of claim 1 wherein the sensor material does not shrink upon first contact with an analyte.

16. The sensor of claim 1 in combination with a means for measuring volume change, wherein the means for measuring volume change relates volume change to concentration of an analyte or group of analytes, wherein the means for measuring volume change comprises a fiber optic, a white light source, and spectrometer configured to measure a reflected spectrum from the sensor material immersed in a solution containing an analyte or group of analytes of interest, the spectrum representative of sensor volume and thus representative of the concentration of an analyte or group of analytes in the solution.

17. A method of monitoring changes in the concentration of an analyte or group of analytes comprising contacting the analyte or group of analytes with a sensor of claim 1, irradiating the sensor with light, and detecting the wavelength of diffracted light, wherein the wavelength of diffracted light corresponds to an increase or decrease in the concentration of the analyte or group of analytes.

18. A method of preparing the gel-based sensor of claim 1 comprising:
   a) polymerizing monomers to form an initial crosslinked gel;
   b) modifying the initial crosslink gel to comprise a covalently bonded molecular recognition moiety, thereby forming the crosslink gel;
   c) combining the crosslinked gel with a volume resetting agent to form the hydrogen bond crosslink between the crosslinked gel and the volume resetting agent; and
   d) covalently crosslinking the volume resetting agent at 0% to about 10% of the repeat units of the crosslinked gel;
   wherein the crosslinked gel and the volume resetting agent form a gel-based sensor.

19. A volume responsive hydrogel sensor comprising:
a crosslinked gel, a volume resetting agent, and a hydrogen bond between the crosslinked gel and the volume resetting agent, wherein:
   a) the crosslinked gel comprises a polyacrylamide modified with a covalently bonded phenylboronic acid moiety that selectively and reversibly binds glucose in a 1:1 ratio, and a covalently bonded drift-reducing agent; and
   b) the volume resetting agent comprises a poly(vinyl alcohol) (PVA) that reversibly bonds the phenylboronic acid moiety;
and wherein an increase in the concentration of glucose in contact with the hydrogel sensor disrupts bonding between the phenylboronic acid moiety of the crosslinked gel and the alcohol moiety of PVA as a function of the concentration to linearly increase the volume of the hydrogel sensor, or a decrease in the concentration of the glucose in contact with the hydrogel sensor reestablishes bonding between the phenylboronic acid moiety of the crosslinked gel and the alcohol moiety of PVA as a function of the concentration to linearly decrease the volume of the hydrogel sensor.

20. A volume responsive hydrogel sensor comprising:
a crosslinked gel, a volume resetting agent (VRA), and a hydrogen bond between the crosslinked gel and VRA, wherein:
   a) the crosslinked gel comprises a polyacrylamide modified with a covalently bonded 1,3-diol moiety that selectively and reversibly binds glucose in a 1:1 ratio; and
   b) the volume resetting agent comprises a second polymer modified with a covalently bonded phenylboronic acid moiety that reversibly bonds the diol moiety;
and wherein an increase in the concentration of glucose in contact with the hydrogel sensor disrupts bonding between the phenylboronic acid moiety of VRA and the diol moiety of the crosslinked gel as a function of the concentration to linearly increase the volume of the hydrogel sensor, or a decrease in the concentration of the glucose in contact with the hydrogel sensor reestablishes bonding between the phenylboronic acid moiety of VRA and the diol moiety of the crosslinked gel as a function of the concentration to linearly decrease the volume of the hydrogel sensor.

21. The sensor of claim 1 comprising a covalent O—C(O)—N crosslink moiety between the crosslinked gel and the volume resetting agent that is up to about 10% of the crosslinked gel's repeat units.

* * * * *